United States Patent [19]

Bair

[11] Patent Number: 4,910,218
[45] Date of Patent: Mar. 20, 1990

[54] PHENANTHRO[2,3-6]THIOPHENE DERIVATIVES, PHARMACEUTICAL COMPOSITIONS AND USE

[75] Inventor: Kenneth W. Bair, Chapel Hill, N.C.

[73] Assignee: Burroughs Wellcome Co., Research Triangle Park, N.C.

[21] Appl. No.: 49,282

[22] Filed: May 12, 1987

Related U.S. Application Data

[63] Continuation-in-part of Ser. No. 801,087, Nov. 22, 1985, abandoned, which is a continuation-in-part of Ser. No. 673,356, Nov. 20, 1984, abandoned.

[30] Foreign Application Priority Data

May 14, 1986 [GB] United Kingdom ............... 8611762
May 14, 1986 [GB] United Kingdom ................. 861761

[51] Int. Cl.$^4$ ................ A61K 31/38; C07D 333/50
[52] U.S. Cl. ................................ 514/443; 514/908; 549/42
[58] Field of Search ................ 549/42; 514/443, 908

[56] References Cited

U.S. PATENT DOCUMENTS 4,219,657  8/1980  Berger et al. ............... 549/43

Primary Examiner—Robert W. Ramsuer
Attorney, Agent, or Firm—Donald Brown

[57] ABSTRACT

The present invention relates to anti tumor compounds of formula (I)

$$ArCH_2R^1 \qquad (I)$$

or a monomethyl or monoethyl ether thereof (the compound of formula (I) including these ethers may contain no more than 29 carbon atoms in total); ethers, esters thereof; acid addition salts thereof; wherein Ar is a fused tetracyclic aromatic ring system comprised of 5-membered and 6-membered rings and contains at least one heteroatom and 3 aromatic rings and a total of no more than 18 ring atoms, or a substituted derivative thereof; the heteroatom is preferably oxygen, sulfur or nitrogen; when it is nitrogen this is substituted by hydrogen, methyl or ethyl; $R^1$ contains not more than eight carbon atoms and is a group

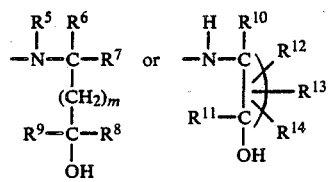

wherein
m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

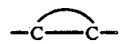

is a five or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

21 Claims, No Drawings

PHENANTHRO[2,3-6]THIOPHENE DERIVATIVES, PHARMACEUTICAL COMPOSITIONS AND USE

This is a continuation-in-part of application Ser. No. 801,087 filed Nov. 22, 1985, now abandoned which is a continuation-in-part of application Ser. No. 673,356 filed Nov. 20, 1984, now abandoned.

The present invention relates to heteropolycyclic aromatic alkanol derivatives which have been found to have biocidal activity. More specifically the invention concerns aminoalkanol derivatives containing a heteropolycyclic aromatic ring system, methods for the synthesis thereof, novel intermediates therefor, pharmaceutical formulations thereof and the use thereof as biocidal agents, particularly antitumor agents.

Accordingly, in a first aspect, the present invention provides a compound of formula (I)

$$ArCH_2R^1 \qquad (I)$$

or a monomethyl or monoethyl ether thereof (the compound of formula (I) including these ethers may contain no more than 29 carbon atoms in total); ethers, esters thereof; acid addition salts thereof; wherein Ar is a fused tetracyclic aromatic ring system comprised of 5-membered and 6-membered rings which contains at least one heteroatom and 3 aromatic rings and a total of no more than 18 ring atoms, or a substituted derivative thereof; the heteroatom is preferably oxygen, sulfur or nitrogen; when it is nitrogen this is substituted by hydrogen, methyl or ethyl; the ring system is optionally substituted by one or two substituents; preferably the ring system is unsubstituted or mono-substituted (the substituents contain not more than four carbon atoms in total when taken together being the same or different and are selected from halogen; cyano; $C_{1-4}$ alkyl or $C_{1-4}$ alkoxy, each optionally substituted by hydroxy or $C_{1-2}$ alkoxy; halogen-substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the ring system is optionally substituted by a group $NR^3R^4$ containing not more than 5 carbon atoms wherein $R^3$ and $R^4$ are the same or different and each is a $C_{1-3}$ alkyl group or $NR^3R^4$ forms a five-or six-membered heterocyclic ring optionally containing one or two additional heteroatoms); $R^1$ contains not more than eight carbon atoms and is a group

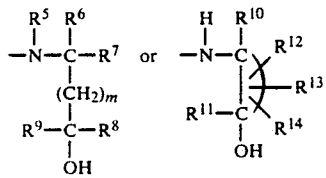

wherein
m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

Specific ring systems included within the scope of the present invention include;

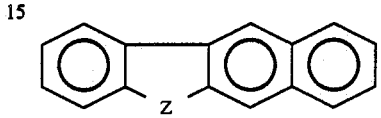

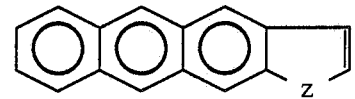

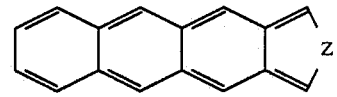

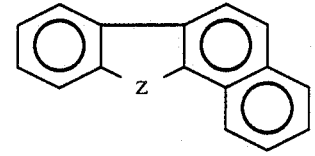

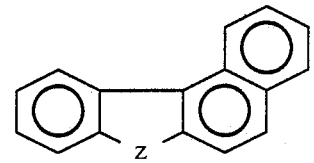

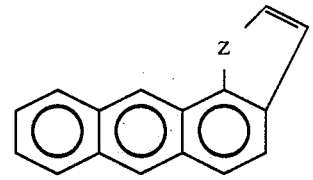

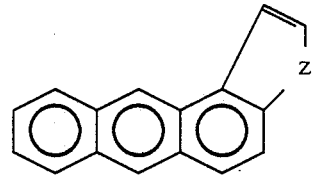

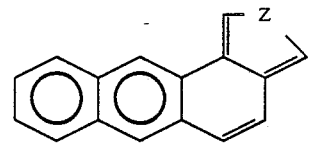

-continued
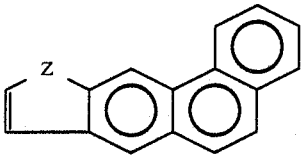
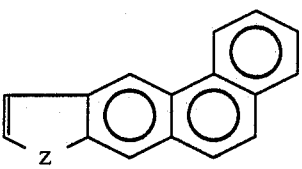
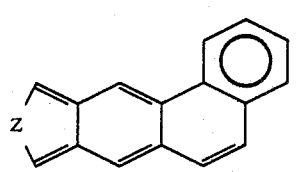
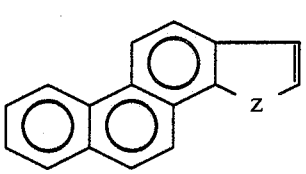
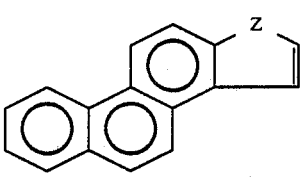
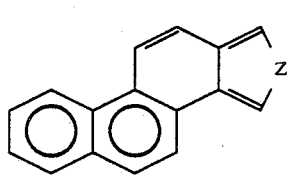
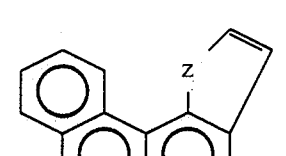
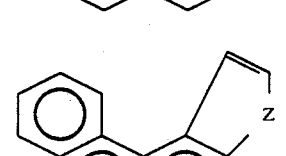
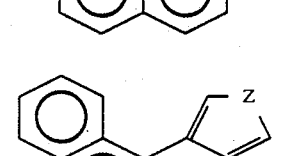
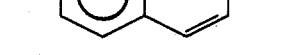
-continued
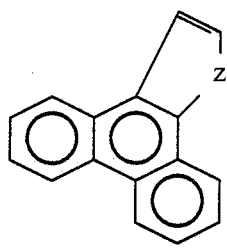
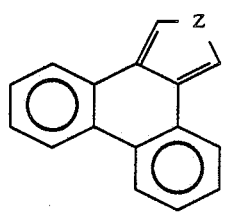
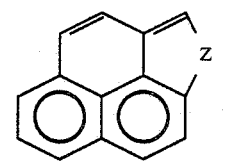
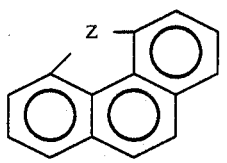
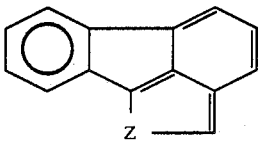
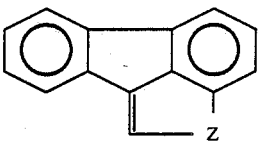
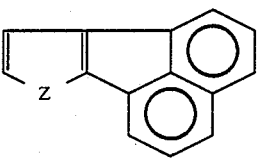
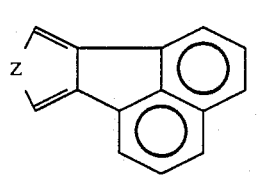

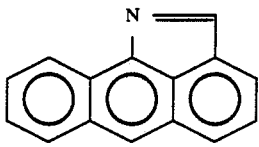
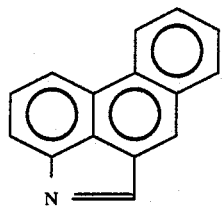
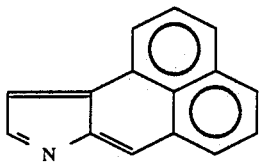
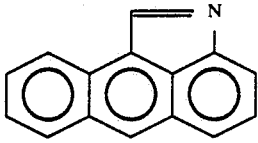
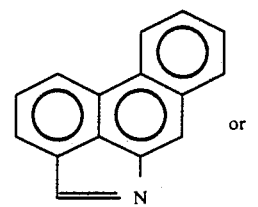
or
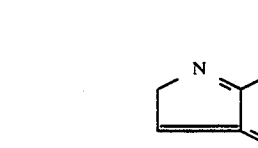
wherein Z is a heteroatom.
Suitably ArCH$_2$R$^1$ or a monomethyl or monethyl ether thereof contains not more than 28 carbon atoms in total.
Suitably Ar is
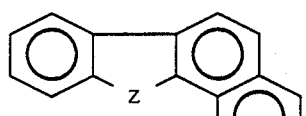
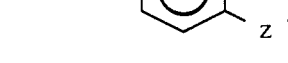
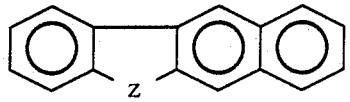
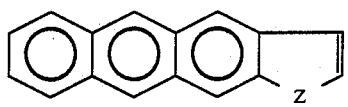
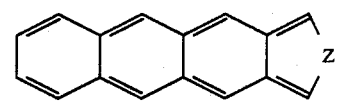
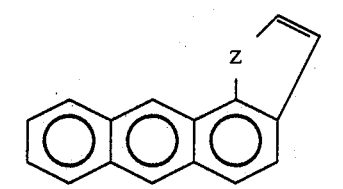
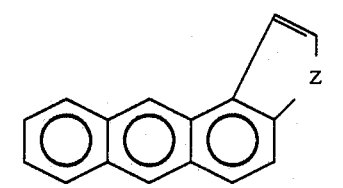
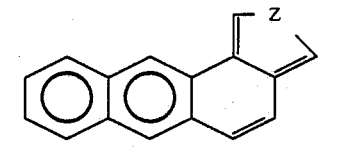
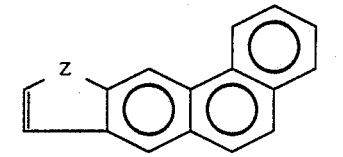
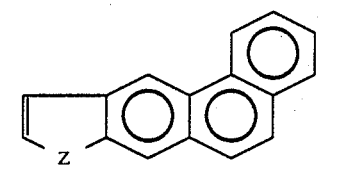
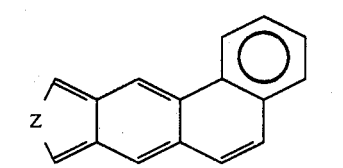
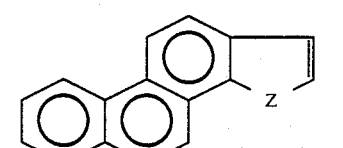

-continued
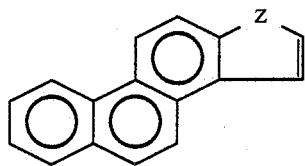
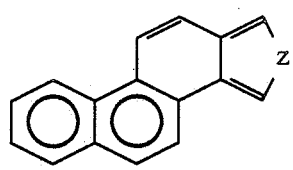
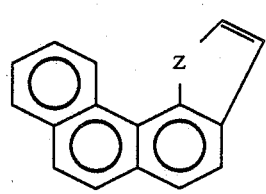
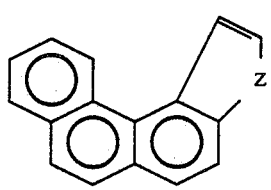
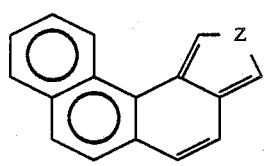
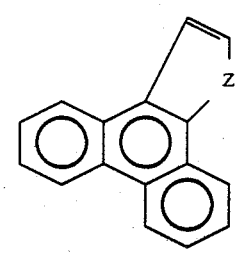
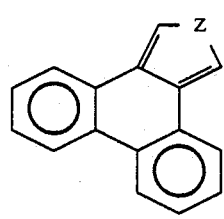
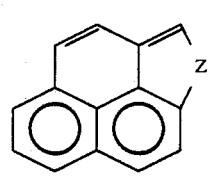
-continued
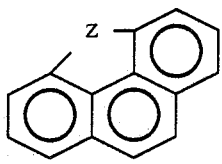
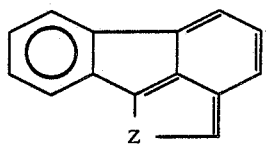
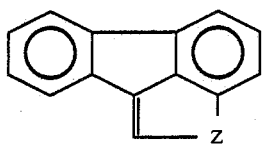
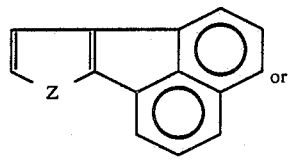
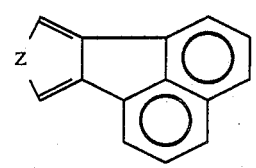 or
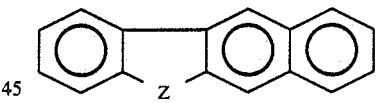
wherein Z is O, S, NH, NCH$_3$, or NEt. More suitably Ar is
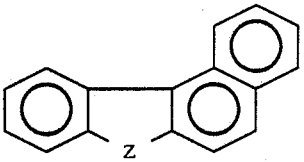
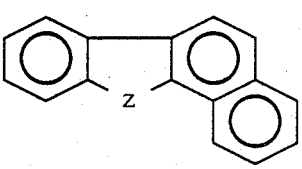
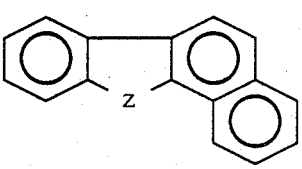
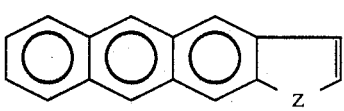

-continued
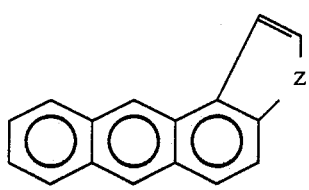
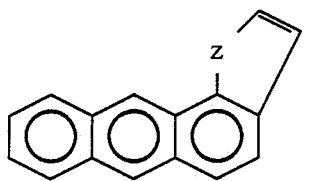
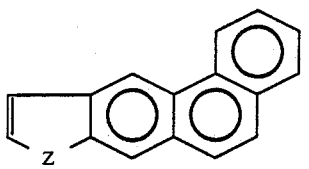
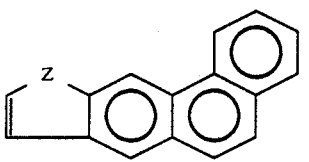
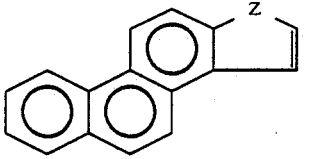
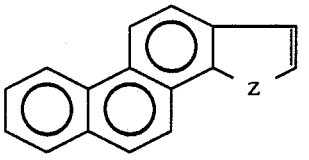
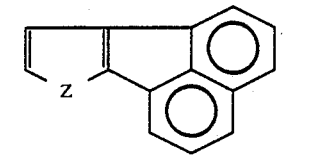
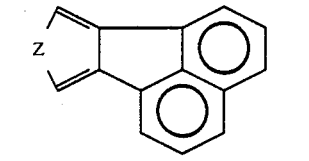
-continued
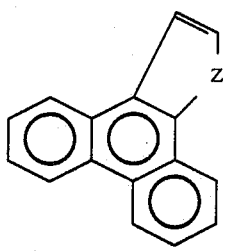
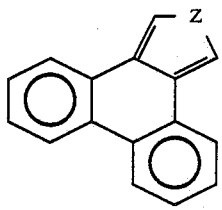
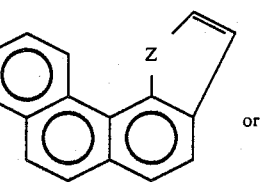
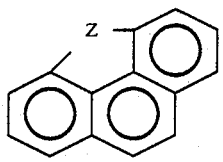 or
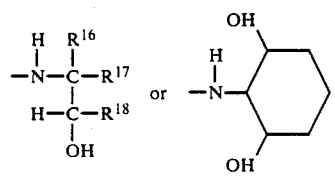
wherein
Z=O, S, NH, NCH$_3$ or NEt;
suitably R$^1$ is
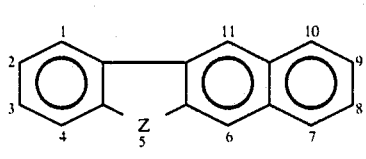
wherein
R$^{16}$ is CH$_2$OH, CH(CH$_3$)OH or CH$_2$CH$_2$OH,
R$^{17}$ is hydrogen, C$_{1-3}$ alkyl or CH$_2$OH,
R$^{18}$ is hydrogen or methyl.
Preferably Ar is
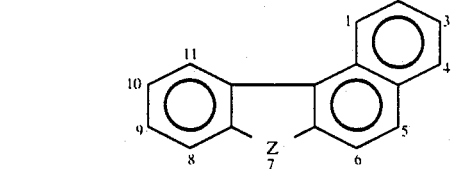

-continued

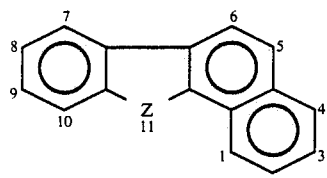

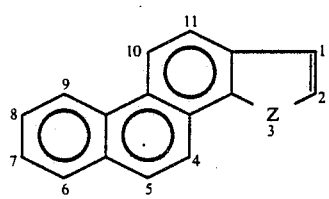

wherein Z=O, S, NH, NCH₃, NEt.
Most preferably Ar is

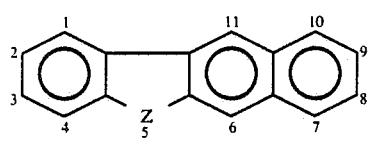

{
Z = O, Benzo[b]naphtho[2,3-d]furan-6-yl-,
Z = O, Benzo[b]naphtho[2,3-d]furan-7-yl-,
Z = O, Benzo[b]naphtho[2,3-d]furan-11-yl-,
Z = S, Benzo[b]naphtho[2,3-d]thiophen-6-yl-,
Z = S, Benzo[b]naphtho[2,3-d]thiophen-7-yl-,
Z = S, Benzo[b]naphtho[2,3-d]thiophen-8-yl-,
Z = NR, 5-Ethyl-5H—benzo[b]carbazol-6-yl-,
Z = NR, 5-Ethyl-5H—benzo[b]carbazol-7-yl-,
}

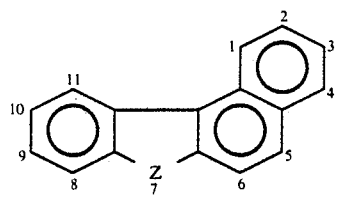

{
Z = O, Benzo[b]naphtho[1,2-d]furan-5-yl-,
Z = S, Benzo[b]naphtho[1,2-d]thiophen-5-yl-,
Z = NR, 7-Methyl-7H—benzo[c]carbazol-10-yl-,
Z = NR, 7-Ethyl-7H—benzo[c]carbazol-10-yl-,
}

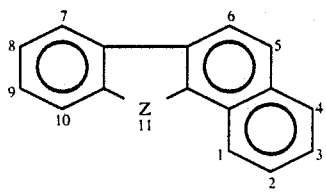

{
Z = O, Benzo[b]naphtho[2,1-d]furan-5-yl-,
Z = S, Benzo[b]naphtho[2,1-d]thiophen-5-yl-,
}

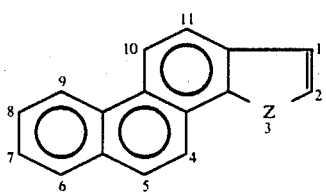

{
Z = O, Phenanthro[1,2-b]furan-11-yl- or
Z = S, Phenanthro[1,2-b]thiophen-11-yl-,
} and $R^{16}$ is CH₂OH or CH(CH₃)OH; $R^{17}$ is hydrogen, methyl, ethyl or CH₂OH.

Most preferably $R^1$ is a diol of the structure

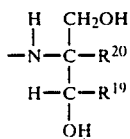

wherein $R^{19}$ is hydrogen or methyl and $R^{20}$ is hydrogen, methyl or ethyl, preferably methyl.

Acid addition salts included within the scope of the present invention are those of the compound of formula (I) and ethers and esters thereof.

Esters and nonpharmaceutically useful salts of the compounds of formula (I) are useful intermediates in the preparation and purification of compounds of formula (I) and pharmaceutically useful acid addition salts thereof, and are therefor within the scope of the present invention. Thus, acid addition salts of the compounds of formula (I) useful in the present invention include but are not limited to those derived from inorganic acids, such as hydrochloric, hydrobromic, sulfuric and phosphoric acids, organic acids such as isethionic (2-hydroxyethylsulfonic), maleic, malonic, succinic, salicylic, tartaric, lactic, citric, formic, lactobionic, pantothenic, methanesulfonic, ethanesulfonic, benzenesulfonic, p-toluenesulfonic, naphthalene-2-sulfonic, and ascorbic acids and amino acids such as glycine.

Acid addition salts particularly useful as biocidal agents are those that are pharmacologically and pharmaceutically acceptable. Thus, suitable acid addition salts include but are not limited to those derived from hydrochloric, methanesulfonic, ethanesulfonic, isethionic, lactic, and citric acids.

The preferred pharmacologically and pharmaceutically acceptable salts are those that are soluble in solvents suitable for parenteral administration, e.g., hydrochlorides, methanesulfonates and isethionates.

Esters of the compounds of formula (I) are derived from carboxylic acids known to those skilled in the art to be suitable for ester formation, and are conveniently those derived from $C_{1-6}$ alkanoic acids or alkanoic acid derivatives, for example, acetic acid, propionic acid, n-butyric acid and iso-butyric acid. The esters may be formed from all or only some of the hydroxy groups contained in the compounds of formula (I). Specific compounds within the scope of formula (I) include:

2-[[(Benzo[b]naphtho[2,1-d]thiophen-5-yl)methyl]amino]-2-methyl-1,3-propanediol,
2[[(Benzo[b]naphtho[2,3-d]furan-6-yl)methyl]amino]-2-methyl-1,3-propanediol,
2-[[(Benzo[b]naphtho[1,2-d]furan-5-yl)methyl]amino]-2-methyl-1,3-propanediol,
2-Methyl-2-[[(7-methyl-7H-benzo[c]carbazol-10-yl)methyl]amino]-1,3-propanediol,
2-[[(Benzo[b]naphtho[2,1-d]furan-5-yl)methyl]amino]-2-methyl-1,3-propanediol,
2[[(Benzo[b]naphtho[2,3-d]furan-7-yl)methyl]amino]-2-methyl-1,3-propanediol,
2-[[(Benzo[b]naphtho[2,3-d]thiophen-6-yl)methyl]amino]-2-methyl-1,3-propanediol,
2-[[(Benzo[b]naphtho[2,3-d]thiophen-8-yl)methyl]amino]-2-methyl-1,3-propanediol,
2-[[(Benzo[b]naphtho[2,3-d]thiophen-7-yl)methyl]mino]-2-methyl-1,3-propanediol,
2-[[(Benzo[b]naphtho[2,3-d]furan-11-yl)methyl]amino]-2-methyl-1,3-propanediol,
2-[[(5-Ethyl-5H-benzo[b]carbazol-7-yl)methyl]amino]-2-methyl-1,3-propanediol,
2-[[(5-Ethyl-5H-benzo[b]carbazol-6-yl)methyl]amino]-2-methyl-1,3-propanediol,
2-[[(Benzo[b]naphtho[1,2-d]thiophen-5-yl)methyl]amino]-2-methyl-1,3-propanediol,
2-Methyl-2-[[(phenanthro[1,2-b]furan-2-yl)methyl]amino]-1,3-propanediol,
2-Methyl-2-[[(phenanthro[1,2-b]furan-11-yl)methyl]amino]-1,3-propanediol,
2-Methyl-2-[[(phenanthro[1,2-b]thiophen-2-yl)methyl]amino]-1,3-propanediol,
2-Methyl-2-[[(phenanthro[1,2-b]thiophen-11-yl)methyl]amino]-1,3-propanediol,
2-Methyl-2-[[(phenanthro[4,3-b]furan-2-yl)methyl]amino]-1,3-propanediol,
2-Methyl-2-[[(phenanthro[4,3-b]thiophen-7-yl)methyl]amino]-1,3-propanediol,
2-Methyl-2-[[(phenanthro[9,10-b]furan-2-yl)methyl]amino]-1,3-propanediol,
2-Methyl-2-[[(phenanthro[9,10-c]thiophen-1-yl)methyl]amino]-1,3-propanediol,
2-[[Acenaphtho[1,2-b]thiophen-8-yl)methyl]amino]-2-methyl-1,3-propanediol,
2-[[Acenaptho[1,2-c]thiophen-7-yl)methyl]amino]-2-methyl-1,3-propanediol,
2-Methyl-2-[[(phenanthro[2,3-b]thiophen-7-yl)methyl]amino]-1,3-propanediol,
2-[[(Benzo[b]naphtho[1,2-d]furan-1-yl)methyl]amino]-1,3-propanediol,
2-Methyl-2-[[(7-methyl-7H-benzo[c]carbazol-8-yl)methyl]amino]-1,3-propanediol,
2-[[(7-Methyl-7H-benzo[c]carbazol-10-yl)methyl]amino]-1,3-propanediol,
(1S,2S)-2-[[(7-Methyl-7H-benzo[c]carbazol-10-yl)methyl]amino]-1-phenyl-1,3-propanediol,
2-Ethoxymethyl-2-[[(7-methyl-7H-benzo[c]carbazol-10-yl)methyl]amino]-1,3-propanediol,
2-Ethyl-2-[[(7-methyl-7H-benzo[c]carbazol-10-yl)methyl]amino]-1,3-propanediol,
2-[[(7-Methyl-7H-benzo[c]carbazol-10-yl)methyl]amino]-2-methyl-1-propanol,
(±)-(2R*,3S*)-2-Methyl-2-[[(7-methyl-7H-benzo[c]carbazol-10-yl)methyl]amino]-1,3-butanediol,
2-Methyl-2-[[(7-methyl-7H-benzo[c]carbazol-5-yl)methyl]amino]-1,3-propanediol,
2-[[(7-Ethyl-7H-benzo[c]carbazol-10-yl)methyl]amino]-2-methyl-1,3-propanediol,
(±)-(2R*,3S*)-2-[[(7-Ethyl-7H-benzo[c]carbazol-10-yl)methyl]amino]-2-methyl-1,3-butanediol,
2-[[(7-Ethyl-7H-benzo[c]carbazol-9-yl)methyl]amino]-2-methyl-1,3-propanediol,
2-[[(7-Ethyl-7H-benzo[c]carbazol-11-yl)methyl]amino]-2-methyl-1,3-propanediol,
2-[[(7-Ethyl-7H-benzo[c]carbazol-8-yl)methyl]amino]-2-methyl-1,3-propanediol,
2-Methyl-2-[[(11-methyl-11H-benzo[a]carbazol-5-yl)methyl]amino]-1,3-propanediol,
(±)-(2R*,S*)-2-Methyl-2-[[(11-methyl-11H-benzo[a]carbazol-5-yl)methyl]amino]-1,3-butanediol,
2-[[(11-Ethyl-11H-benzo[a]carbazol-8-yl)methyl]amino]-2-methyl-1,3-propanediol,
2-[[(11-Ethyl-11H-benzo[a]carbazol-9-yl)methyl]amino]-2-methyl-1,3-propanediol,
2-[[(Benzo[b]naphtho[1,2-d]furan-10-yl)methyl]amino]-2-methyl-1,3-propanediol,
2-Methyl-2-[[(phenanthro[1,2-b]thiophen-5-yl)methyl]amino]-1,3-propanediol,
2-Methyl-2-[[(phenanthro[1,2-b]furan-5-yl)methyl]amino]-1,3-propanediol,
(±)-(2R*,3S*)-2-[[(Benzo[b]naphtho[2,3-d]furan-6-yl)methyl]amino]-2-methyl-1,3-butanediol,
2-Methyl-2-[[(phenanthro[3,2-b]thiophen-7-yl)methyl]amino]-1,3-propanediol,
2-Methyl-2-[[(3-methyl-3H-naphth[1,2-g]indol-1-yl)methyl]amino]-1,3-propanediol,
(±)-(2R*,3S*)-2-Methyl-2-[[(3-methyl-3H-naphth[1,2-g]indol-1-yl)methyl]amino]-1,3-butanediol,
2-Methyl-2-[[(3-methyl-3H-naphth[2,3-e]indol-11-yl)methyl]amino]-1,3-propanediol,
2-Methyl-2-[[(1-methyl-1H-naphth[2,3-g]indol-3-yl)methyl]amino]-1,3-propanediol,
2-Methyl-2-[[(1-methyl-1H-napth[2,3-g]indol-5-yl)methyl]amino]-1,3-propanediol,
2-Methyl-2-[[(1-methyl-1H-[1]benzothieno[2,3-g]indol-3-yl)methyl]amino]-1,3-propanediol,
2-[[(6-Ethyl-1,6-dihydro-1-methylpyrrolo[3,2-c]carbazol-3-yl)methyl]amino]-2-methyl-1,3-propanediol,
2-Methyl-2-[[(1-methyl-1H-benzofuro[2,3-g]indol-3-yl)methyl]amino]-1,3-propanediol,
2-Methyl-2-[[(3-methyl-3H-[1]benzothieno[2,3-e]indol-1-yl)methyl]amino]-1,3-propanediol,
2-Hydroxymethyl-2-[[(7-methyl-7H-benzo[c]carbazol-10-yl)methyl]amino]-1,3-propanediol,
2-Hydroxymethyl-2-[[(7-methyl-7H-benzo[c]carbazol-5-yl)methyl]amino]-1,3-propanediol,
2-[[(Benzob]naphtho[2,3-d]thiophen-4-yl)methyl]amino]-2-methyl-1,3-propanediol,
2-[[(Benzo[b]naphtho[1,2-d]thiopen-10-yl)methyl]amino]-2-methyl-1,3-propanediol,
(±)-3-Methoxy-2-methyl-2-[[(7-methyl-7H-benzo[c]carbazol-10-yl)methyl]amino]-1,3-propanediol,
[1,1-Bis-(methoxymethyl)ethyl]-[(7-methyl-7H-benzo[c]carbazol-10-yl)methyl]amine,
2-Isopropyl-2-[[(7-methyl-7H-benzo[c]carbazol-10-yl)methyl]amino]-1,3-propanediol,
2β-[[(7-Methyl-7H-benzo[c]carbazol-10-yl)methyl]amino]-1α,3α-cyclohexanediol,
2-[[(7-Methyl-7H-benzo[c]carbazol-10-yl)methyl]amino]-2-pentyl-1,3-propanediol,
3-Methoxy-2-(methoxymethyl)-2-[[(7-methyl-7H-benzo[c]carbazol-10-yl)methyl]amino]propanol, 2-Methyl-2-[[(7-methyl-7H-benzo[c]carbazol-10-yl)methyl]amino]-1,4-butanediol,
2-[[(10-Methyl-10H-[1]benzothieno[3,2-b]indol-6-yl)methyl]amino]-2-methyl-1,3-propanediol,
2-[[(10-Methyl-10H-[1]benzothieno[3,2-b]indol-3-yl)methyl]amino]-2-methyl-1,3-propanediol; ethers, esters thereof; acid addition salts thereof.

Of these specific examples of compounds of formula (I), the most preferred compounds are 2-methyl-2-[[(7-methyl-7H-benzo[c]carbazol-10-yl)methyl]amino]-1,3-propanediol; and 2-[[(benzo[b]naphtho[2,1-d]furan-5-yl)methyl]amino]-2-methyl-1,3-propanediol; ethers, esters thereof; acid addition salts thereof. The compounds of formula (I) and their ethers, esters and salts thereof may be prepared by any method known in the art for the preparation of compounds of analogous structure. Thus, the compounds of formula (I) may, for example, be prepared by any of the methods defined below.

1. The reduction of a compound of formula (II) or (IIa)

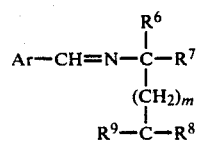    (II)

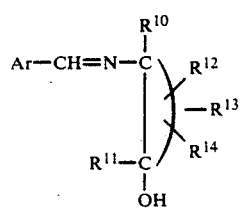    (IIa)

wherein $R^2$-$R^4$ and $R^6$-$R^{14}$ are as hereinbefore defined or a suitably protected derivative thereof followed by deprotection where appropriate.

The conditions and reagents for such a reaction are well known to those skilled in the art, and any such conditions/reagents may be employed. The conversion of the compound of formula (II) or (IIa) or suitably protected derivatives thereof may be carried out by a reducing agent followed by deprotection if necessary. The reduction is conveniently carried out by a metal hydride such as lithium aluminum hydride, sodium borohydride, sodium cyanoborohydride, or by catalytic hydrogenation, conveniently by hydrogen in the presence of a metal catalyst such as palladium or platinum, or equivalent reagents as outlined by J. March, *Advanced Organic Chemistry*, 2nd ed., pages 819–820, McGraw Hill, N.Y., 1977. The reduction is suitably carried out with a compound of formula (II) or (IIa) in solution in an inert solvent or mixture of solvents compatible with the reducing agent, at a nonextreme temperature, for example, between 0° and 80° C., conveniently at room temperature.

In the case of lithium aluminum hydride and like reagents, suitable solvents include ethers (for example tetrahydrofuran, diethyl ether and 1,2-dimethoxyethane) optionally in the presence of a hydrocarbon cosolvent (for example, toluene, benzene or hexane).

In the case of sodium borohydride and like reagents, suitable solvents include alcohols (for example ethanol, methanol or isopropanol) optionally in the presence of a hydrocarbon cosolvent (for example toluene, benzene or hexane) or an ether cosolvent (for example diethyl ether or tetrahydrofuran).

In the case of sodium cyanoborohydride and like reagents, suitable solvents include those described for sodium borohydride and in the presence of an acid conveniently glacial acetic acid or ethanolic hydrochloric acid as outlined in, for example, R. Hutchins et al., *Organic Preparations and Procedures International* 11, 201 (1979).

In the case of catalytic hydrogenation, suitable solvents include alcohols (for example methanol and ethanol) optionally in the presence of a hydrocarbon cosolvent (for example toluene or benzene) or ether cosolvent (for example, diethyl ether or tetrahydrofuran) in the presence of an acid (for example, glacial acetic acid or ethanolic hydrochloric acid) or in glacial acetic acid.

Protected derivatives of compounds of formula (II) or (IIa) are conveniently used when lithium aluminum hydride is employed as the reducing agent. Convenient protecting groups are compatible with the reducing agent utilized and are readily removed under nondestructive conditions, for example benzyl, tetrahydropyranyl and isopropylidene ethers.

It is often convenient not to isolate the compound of the formula (II) or (IIa) but to react a compound of the formula (III) with a compound of the formula (IV) or (IVa):

    (III)

    (IV)

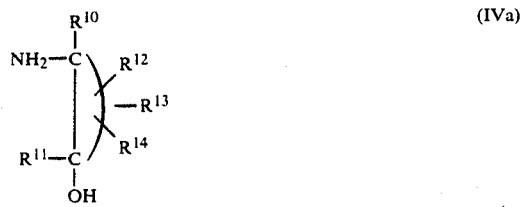    (IVa)

wherein Ar and $R^2$-$R^4$ and $R^6$-$R^{14}$ are as defined hereinbefore and reduce the compound of formula (II) or (IIa) so formed in situ. The reaction of the compounds of formulae (III) and (IV) or (IVa) is again suitably carried out using conditions and reagents which are well known to those skilled in the art, for example, in the presence of an acid, such as a sulfonic acid, i.e., p-toluenesulfonic acid, in an appropriate inert solvent, such as an aromatic hydrocarbon, suitably toluene, with azeotropic removal of water followed by treatment with the reducing agent in an appropriate solvent, suitably ethanol or methanol. Alternatively, the compound of formula (II) or (IIa) formed under equilibrium conditions in appropriate solvents can be reduced in situ with an appropriate reducing agent, suitably sodium cyanoborohydride. The compound of formula (III) may be in the form of a protected aldehyde, for example, an acetal, which liberates the aldehyde function under the reaction conditions.

In turn, a compound of formula (III) can be synthesized by reacting the appropriate aromatic heteropolycycle with a formylating agent such as that generated by the reaction between SnCl$_4$ and Cl$_2$CHOCH$_3$ or equivalent reagents, for example, according to the method of A. Rieche et al., *Chem. Ber.* 93, 88 (1960), or with other standard formylating reagents/procedures known to the art, for example, the Gatterman-Koch reaction (CO/HCl/AlCl$_3$/CuCl), the Gatterman reaction (HCN/HCl/ZnCl$_2$), and the Vilsmeier reaction (POCl$_3$/PhN(Me)CHO, or POCl$_3$/Me$_2$NCHO) (J. March, vide supra, pages 494-497).

A compound of formula (III) may also be prepared from an appropriate aromatic heteropolycycle substituted by a suitable functional group such as (but not limited to) esters, CH$_2$OH, CHBr$_2$, CH$_3$, COCH$_3$, COOH, or CN, and converting this functional group to an aldehyde group by methods well known to those skilled in the art.

Where the aromatic heteropolycycle bears *substituents*, the compound of formula (III) may be prepared by a variety of methods known in the art of organic chemistry depending on the nature of the substituent on the heteropolycyclic ring. For example, if the substituent(s) be halogen, the starting materials may be prepared by direct treatment of the aromatic heteropolycycle with a halogenating agent (e.g., Cl$_2$, Br$_2$ or SO$_2$Cl$_2$) or indirectly by such routes as the Sandmeyer reaction (H. H. Hodgson, *Chem. Rev.* 40, 251 (1947). If the substituent(s) be alkyl, the aromatic heteropolycycle may be reacted with the appropriate reagents under Friedel-Crafts reaction conditions (G. A. Olah, *Friedel Crafts and Related Reactions*, Vols. 1-3, Interscience, New York, N.Y., 1963-1965).

In appropriate cases, the compounds of formula (IV) or (IVa) and ethers thereof also may be prepared by methods known in the art, for example, by the reaction of a compound of the formula (V) or (Va)

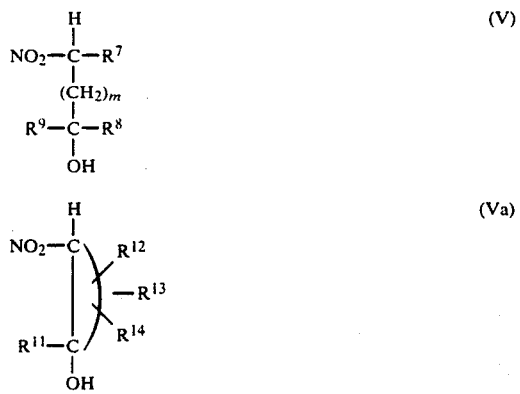

(or ethers thereof) wherein R$^7$-R$^9$ and R$^{11}$-R$^{14}$ and m are as hereinbefore defined with an appropriate aldehyde, conveniently acetaldehyde or formaldehyde (as in B. M. Vanderbilt and H. B. Hass, *Ind. Eng. Chem.* 32, 34 (1940)) followed by reduction (as outlined in J. March, vide supra, pages 1125-1126), conveniently by hydrogen and a metal catalyst (for example, a platinum-containing catalyst) in an appropriate solvent, conveniently glacial acetic acid.

2. The reduction of a compound of the formula (VI) or (VIa)

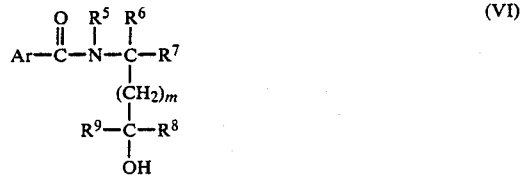

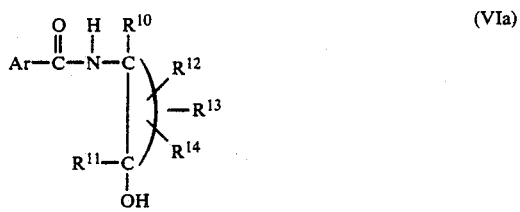

wherein Ar and R$^2$-R$^{14}$ and m are as hereinbefore defined and the hydroxy groups are optionally protected, followed by deprotection of the hydroxy groups where appropriate. The reduction may be carried out by standard reducing agents known for carrying out this type of reduction (as outlined in J. March, vide supra page 1122), for example, a hydride reagent such as lithium aluminium hydride in an inert solvent, such as an ether, i.e., tetrahydrofuran, at a non-extreme temperature, for example, at between 0° C. and 100° C. and conveniently at the reflux temperature of the ether. The compound of formula (VI) or (VIa) may be formed by the reaction of the appropriate acid (ArCOOH) or a suitable reactive acid derivative thereof (as outlined in J. March, vide supra, pages 382-390), for example, an acid halide, in an inert solvent with an amine of formula (IV) or (IVa) in which the hydroxy groups are optionally protected, for example, when the compound of formula formula (IV) or (IVa) is a diol, by an isopropylidene group. The compound of formula (VI) or (VIa) so formed is suitably reduced in situ and deprotected if necessary to give a compound of formula (I). The compounds of the formula ArCOOH can be prepared by methods well known to those skilled in the art.

3. The reaction of a compound ArCH$_2$L (wherein Ar is as hereinbefore defined and L is a leaving group) with a compound of formula (IV) or (IVa) as hereinbefore defined. Suitable leaving groups are those defined by J. March, vide supra, pages 325-331, and include halogens such as chlorine and bromine and sulfonic acid derivatives such as p-toluenesulfonate. The reaction is suitably carried out in an appropriate solvent, such as a dipolar aprotic solvent or alcohol at a non-extreme temperature, for example 50°-100°. The compounds of the formula ArCH$_2$L can be prepared by methods well known to those skilled in the art.

There is therefore provided, as a further aspect of the invention, a method for the preparation of a compound of formula (I) comprising any method known for the preparation of analogous compounds, in particular those methods defined in (1) to (3) hereinabove.

The compounds of this invention have biocidal activity, e.g., are toxic to certain living cells which are detrimental to mammals, for example pathogenic organisms and tumor cells. While the compounds herein have biocidal activity, it should be appreciated that the range and level of activity may vary from compound to compound, and therefore the compounds are not necessarily equivalent.

This toxicity to pathogenic organisms has been demonstrated by activity against viruses (e.g., *Herpes simplex* 1/vero), fungi (e.g., *Candida albicans*), protozoa (e.g., *Eimeria tenella* and *Trichomonas vaginalis*), bacteria (e.g., *Mycoplasma smegmatis* and *Streptococcus pyogenes*), and helminths (e.g., *Nippostrongylus brasiliensis*). The antitumor activity of compounds of formula (I) has been demonstrated in a number of recognized screens and primarily by activity against ascitic P388 leukemia.

Preferred compounds of formula (I) are those which have antitumor activity. The activity against ascitic tumors, including P388, is evidenced by reduction of tumor cell number in mammals (for example, mice bearing ascitic tumors) and consequent increase in survival duration as compared to an untreated tumor-bearing control group. Antitumor activity is further evidenced by measurable reduction in the size of solid tumors following treatment of mammals with the compounds of this invention compared to the tumors of untreated control tumor-bearing animals. Compounds of formula (I) are active against murine tumors such as lymphocytic leukemia P388, lymphocytic leukemia L1210, melanotic melanoma B16, P815 mastocytoma, MDAY/D2 fibrosarcoma, colon 38 adenocarcinoma, M5076 rhabdomyosarcoma and Lewis lung carcinoma.

Activity in one or more of these tumor tests has been reported to be indicative of antitumor activity in man (A. Goldin et al., in *Methods in Cancer Research* ed. V. T. DeVita Jr. and H. Busch, 16 165, Academic Press, N.Y. 1979).

There are sublines of P388 which have been made resistant to the following clinically useful agents: cytosine arabinoside, doxorubicin, cyclophosphamide, L-phenylalanine mustard, methotrexate, 5-fluorouracil, actinomycin D, cis-platin and bis-chloroethylnitrosourea. Compounds of this invention show potent activity against these drug-resistant tumors using the procedure for P388 above.

Compounds of formula (I) have also been found to be active against human tumor cells in primary cultures of lung, ovary, breast, renal, melanoma, unknown primary, gastric, pancreatic, mesothelioma, myeloma, and colon cancer. As used herein "cancer" is to be taken as synonymous with "malignant tumor" or more generally "tumor" unless otherwise noted. This is a procedure in which the prevention of tumor cell colony formation, i.e., tumor cell replication, by a drug has been shown to correlate with clinical antitumor activity in man (D. D. Von Hoff et al., *Cancer Chemotherapy and Pharmacology* 6, 265 (1980); S. Salmon and D. D. Von Hoff, *Seminars in Oncology*, 8, 377 (1981)).

Compounds of formula (I) which have been found to have antitumor activity intercalate in vitro with DNA (this property is determined by viscometric methods using the procedure of W. D. Wilson et al., *Nucleic Acids Research* 4, 2697 (1954)) and a log P as calculated by the method of C. Hansch and A. Leo in *Substituent Constants for Correlation Analysis in Chemistry and Biology*, John Wiley and Sons, N.Y., 1979, lying in the range between −2.0 and +2.5.

As has been described above, the compounds of the present invention are useful for the treatment of animals (including humans) bearing susceptible tumors. The invention thus further provides a method for the treatment of tumors in animals, including mammals, especially humans, which comprises the administration of a clinically useful amount of compound of formula (I) in a pharmaceutically useful form, once or several times a day or other appropriate schedule, orally, rectally, parenterally, or applied topically.

In addition, there is provided as a further, or alternative, aspect of the invention, a compound of formula (I) for use in therapy, for example as an antitumor agent.

The amount of compound of formula (I) required to be effective as a biocidal agent will, of course, vary and is ultimately at the discretion of the medical or veterinary practitioner. The factors to be considered include the condition being treated, the route of administration, the nature of the formulation, the mammal's body weight, surface area, age, general condition and the particular compound to be administered. A suitable effective antitumor dose of a compound of formula (I) is in the range of about 0.1 to about 120 mg/kg body weight, preferably in the range of about 1.5 to 50 mg/kg, for example, 10 to 30 mg/kg. The total daily dose may be given as a single dose, multiple doses, e.g., two to six times per day, or by intravenous infusion for a selected duration. For example, for a 75 kg mammal the dose range would be about 8 to 9000 mg per day, and a typical dose would be about 2000 mg per day. If discrete multiple doses are indicated, treatment might typically be 500 mg of a compound of formula (I) given 4 times per day in a pharmaceutically useful formulation.

While it is possible for the active compound (defined herein as a compound of formula (I), or ether, ester or salt thereof) to be administered alone, it is preferably to present the active compound in a pharmaceutical formulation. Formulations of the present invention, for medical use, comprise an active compound together with one or more pharmaceutically acceptable carriers thereof and optionally other therapeutical ingredients. The carrier(s) must be pharmaceutically acceptable in the sense of being compatible with the other ingredients of the formulation and not deleterious to the recipient thereof.

The present invention, therefor, further provides a pharmaceutical formulation comprising a compound of formula (I) (in the form of the free base, ether or ester derivative or a pharmaceutically acceptable acid addition salt thereof) together with a pharmaceutically acceptable carrier therefor.

There is also provided a method for the preparation of a pharmaceutical formulation comprising bringing into association a compound of formula (I), an ether, ester or pharmaceutically acceptable salt thereof, and a pharmaceutically acceptable carrier therefor.

While the antitumor activity of the compounds of formula (I) is believed to reside in the free base, it is often convenient to administer an acid addition salt of a compound of formula (I).

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine the active compound in a free-flowing form such as a powder or granules, optionally mixed with a binder, lubricant, inert diluent, surface active agent or dispersing agent. Molded tablets may be made by molding in a suitable machine, a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavorings, an agent to retard crystallization of the sugar or an agent to increase the solubility of any other ingredient, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of formula (I) that is isotonic with the blood of the recipient. Thus, such formulations may conveniently contain distilled water, 5% dextrose in distilled water or saline and a pharmaceutically and pharmacologically acceptable acid addition salt of a compound of formula (I) that has an appropriate solubility in these solvents, e.g., the hydrochloride, isethionate and methanesulfonate salts, preferably the latter.

Useful formulations also comprise concentrated solutions or solids containing the compound of formula (I) which upon dilution with an appropriate solvent give solutions suitable for parental administration above.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

The following examples are provided by the way of illustration of the present invention and should in no way be construed as a limitation thereof.

GENERAL COMMENTS

All solvents were reagent grade and used without further purification with the following exceptions. THF was dried by distillation from Na/K alloy under nitrogen ($N_2$) and used immediately. Toluene ($PhCH_3$) was distilled from $CaH_2$ under $N_2$ and stored over 3Å molecular sieves. Chemicals used were reagent grade and used without purification unless noted. The full name and address of the suppliers of the reagents and chemicals is given when first cited. After this, an abbreviated name is used.

Preparative HPLC was carried out on a Water's Prep LC/System 500A machine using two 500 g silica gel ($SiO_2$) cartridges unless otherwise noted. Plugs of $SiO_2$ used for purifications were "flash chromatography" $SiO_2$ (Merck & Co., Inc., Merck Chemical Division, Rahway, N.J. 07065, Silica Gel 60, 230–400 mesh). In this procedure, an appropriate volume sintered glass funnel was filled approximately ¾ full with the $SiO_2$ and packed evenly by tapping the outside of the funnel. A piece of filter paper was then placed on top of the $SiO_2$ and a solution of the material to be purified applied evenly to the top. Gentle suction through a filter flask moved the eluting solvent through the plug rapidly. The appropriate size fractions were combined as needed and further manipulated.

General procedures are described in detail. Analogous procedures show melting point (mp), recrystallization solvents, and elemental analyses (all elements analyzing within a difference of $\leq 0.4\%$ of the expected value). Any changes to the procedure such as solvent, reaction temperature, reaction time, or workup are noted.

NMR ($^1H$, $^{13}C$), IR and MS data of all new products were consistent with the expected and proposed structures. The positions assigned to structural isomers were unequivocally determined by a number of NMR techniques. All final products were dried in a vacuum over at 20 mm Hg pressure at the temperature indicated overnight (12–16 h). All temperatures are in degrees Celsius. Other abbreviations used are: room temperature (RT), absolute (abs.), round bottom flask (RB flask), minutes (min), hours (h).

EXAMPLE 1

2-[[(Benzo[b]naphtho[2,1-d]thiophen-5-yl)methyl-]amino]-2-methyl-1,3-propanediol methanesulfonate To a 3-necked RB flask equipped with magnetic stirring bar, condenser, thermometer, Dean-Stark trap and $N_2$ inlet line with bubbler was added benzo[b]naphtho[2,1-d]thiophene-5-carbaldehyde (H. G. Pars Pharmaceutical Laboratories, Inc., 763 Concord Avenue, Cambridge, Mass., 02138, 4.94 g, 18.83 mmol), 2-amino-2-methyl-1,3-propanediol (Aldrich Chemical Co, P. O. Box 2060, Milwaukee, Wis., 53201, 1.98 g, 18.83 mmol), p-toluenesulfonic acid monohydrate (Aldrich, 0.1 g) and $PhCH_3$ (200 mL). The mixture was stirred at reflux with removal of $H_2O$ for 2.5 h (or until no $H_2O$ was collected). Most of the $PhCH_3$ was then removed by distillation. The mixture was then cooled in an ice bath and diluted with abs. EtOH (200 mL) and further cooled. Solid $NaBH_4$ (MCB Manufacturing Chemists, Inc., 2909 Highland Ave., Cincinnati, Ohio, 45212, 0.712 g, 18.83 mmol) was added in one portion to the reaction mixture. The ice bath was then removed, the reaction mixture allowed to warm to RT and stirred overnight. The reaction was then acidified with 10% HCl and the solvents removed by rotary evaporation. The crude solid was shaken with 1 N HCl (300 mL) filtered, washed with 1 N HCl (300 mL), sucked semi-dry, and washed with $Et_2O$ (300 mL). The material was dissolved in $CH_3OH$ (200 mL), filtered and basified with 1N NaOH solution (1 L). A white solid formed which was extracted with EtOAc (3×500 mL). The EtOAc washings were combined, filtered, washed with saturated NaCl (3×500 mL), dried ($K_2CO_3$), filtered and concentrated by rotary evaporation to give a white solid. This was dissolved in a mixture of abs. EtOH (200 mL) and CH$_3$SO$_3$H (99.5%, Morton Thiokol, Inc. - Alfa Products, P. O. Box 299, 152 Andover Street, Danvers, Mass., 01923, 3 mL), filtered and diluted to 4 L with a mixture of Et$_2$/hexane (1:1). This material was then recrystallized (EtOH/hexane, 1:3) to give 2-[[(benzo[b]naphtho[2,1-d]thiophen-5-yl)methyl]amino]-2-methyl-1,3-propanediol methanesulfonate, mp 221°–222° (C,H,N,S).

Alternatively, the crude reaction mixture could be treated with 1N NaOH solution or H$_2$O before the solvents were removed. After thorough washing with H$_2$O and drying the resulting crude solid was converted to its acid addition salt with either ethanolic HCl or methanesulfonic acid. Recrystallization of the resulting salt can be accomplished using i-PrOH, CH$_3$OH, EtOH or other alcohols alone or in combination with a nonpolar solvent such as Et$_2$O, hexane, PhCH$_3$ or other inert solvents. A larger ratio of amine to aldehyde (e.g., 2:1) can also be used to increase the yield of the final products.

EXAMPLE 2

2-[[(Benzo[b]naphtho[2,3-d]furan-6-yl)methyl]amino]-2-methyl-1,3-propanediol

2A. Benzo[b]naphtho[2,3-d]furan-6-carbaldehyde

2B. Benzo[b]naphtho[2,3-d]furan-11-carbaldehyde

Benzo[b]naphtho[2,3-d]furan (H. G. Pars Pharmaceutical Laboratories, Inc.) was formylated using the procedure of A. Rieche et al., Chem. Ber. 93, 88 (1960). The crude aldehyde appeared to be mainly one isomer accompanied by a small amount of a second aldehyde by TLC. Purification by chromatography (SiO$_2$, PhCH$_3$) followed by recrystallization (CH$_2$Cl$_2$/hexane) gave the main component in 58% yield identified using NMR techniques to be benzo[b]naphtho[2,3-d]furan-6-carbaldehyde, (2A) mp 169°–171.5°, (C,H). The minor component, obtained in 3.4% yield was shown by NMR to be benzo[b]naphtho[2,3-d]furan-11-carbaldehyde, mp 128°–132°, (C,H), (PhCH$_3$/hexane).

2C. 2-[[(Benzo[b]naphtho[2,3-d]furan-6-yl)methyl]amino]-2-methyl-1,3-propanediol methanesulfonate·0.4 H$_2$O Using the reductive amination procedure described in Example 1, benzo[b]naphtho[2,3-d]furan-6-carbaldehyde (2A) and 2-amino-2-methyl-1,3-propanediol (Aldrich) gave a 64.7% yield of 2-[[(benzo[b]naphtho[2,3-d]furan-6-yl)methyl]amino]-2-methyl-1,3-propanediol methanesulfonate·0.4 H$_2$O, mp 187°–190°, (C,H,N,S), (EtOH/Et$_2$O).

EXAMPLE 3

2-[[(Benzo[b]naphtho[1,2-d]furan-5-yl)methyl]amino]-2-methyl-1,3-propanediol

3A. Benzo[b]naphtho[1,2-d]furan-5-carbaldehyde

Benzo[b]naphtho[1,2-d]furan (H. G. Pars Pharmaceutical Laboratories, Inc.) was formylated using the procedure of A. Rieche et al., Chem. Ber. 93, 88 (1960). The crude aldehyde appeared to be only one isomer by TLC. Purification by chromatography (SiO$_2$, PhCH$_3$) followed by recrystallization (CH$_2$Cl$_2$/hexane) gave pure material (39% yield), identified using NMR techniques to be benzo[b]naphtho[1,2-d]furan-5-carbaldehyde, mp 143°–145°, (C,H).

3B. 2-[[(Benzo[b]naphtho[1,2-d]furan-5-yl)methyl]amino]-2-methyl-1,3-propanediol methanesulfonate Using the reductive amination procedure described in Example 1, benzo[b]naphtho[1,2-d]furan-5-carbaldehyde (3A) and 2-amino-2-methyl-1,3-propanediol (Aldrich) gave a 72.1% yield of 2-[[(benzo[b]naphtho[1,2-d]furan-5yl)methyl]amino]-2-methyl-1,3-propanediol methanesulfonate, mp 215°–217°, (C,H,N,S), (EtOH/Et$_2$O).

EXAMPLE 4

2-Methyl-2-[[(7-methyl-7H-benzo[c]carbazol-10-yl)methyl]amino]-1,3-propanediol 4A. 7-Methyl-7H-benzo[c]carbazole To a RB flask equipped with magnetic stirring bar, reflux condenser and N$_2$ inlet line with bubbler was added 7H-benzo[c]carbazole (H. G. Pars Pharmaceutical Laboratories, Inc., 6.6 g, 30.4 mmol) and dry THF (250 mL). To the flask was added in one portion potassium t-butoxide (Aldrich, 4.2 g, 37.4 mmol). Dimethylsulfate (Aldrich, 7.56 g, 60.0 mmol, 5.9 mL) was added dropwise to the solution and the mixture stirred for 15 min. TLC (SiO$_2$/PhCH$_3$) showed the reaction to be complete. The reaction mixture was then poured into a 1 N NaOH solution (2 L) and stirred. The white solid which formed was collected by filtration, washed with H$_2$O (3×500 ml), sucked semidry, dissolved in PhCH$_3$ (300 ml) and eluted through a plug of SiO$_2$ (5×5 cm) using PhCH$_3$ as the eluting solvent. Appropriate fractions were combined and the solvent removed to give a crude white product. This material was dissolved in CH$_2$Cl$_2$ (400 mL), filtered and diluted to 1 L with hexane. The mixture was concentrated to 500 mL by rotary evaporation. A white solid formed which was filtered, washed with pentane and dried in a vacuum to give 5.0 g of 7-methyl-7H-benzo[c]carbazole, mp 116°–118°, (C,H,N). A further 1.06 g of product was obtained on standing and further concentration of the filtrate to give a combined yield of 87.3%.

4B. 7-Methyl-7H-benzo[c]carbazole-10-carbaldehyde 4C. 7-Methyl-7H-benzo[c]carbazole-5-carbaldehyde 4D. 7-Methyl-7H-benzo[c]carbazole-8-carbaldehyde 7-Methyl-7H-benzo[c]carbazole (4A) was formylated using the procedure of A. Rieche et al., Chem. Ber. 93, 88 (1960). TLC (SiO$_2$/PhCH$_3$) showed that the crude mixture contained two aldehydes. Column chromatography (SiO$_2$/PhCH$_3$) followed by crystallization (CH$_2$Cl$_2$/pentane) gave each of the aldehydes in isomerically pure form. A total of 3.83 g (59.1%) of the more mobile main component, 7-methyl-7H-benzo[c]carbazole-10-carbaldehyde, mp 164°–165°, (C,H,N). A total of 0.55 g (8%) of a minor, less mobile component was identified by NMR as 7-methyl-7H-benzo[c]carbazole-5-carbaldehyde, mp 210°–213° (C,H,N).

Formylation of a 100 g batch of 7-methyl-7H-benzo[c]carbazole gave similar yields of 4B and 4C. An additional aldehyde was isolated in 3.8% yield which was shown to be 7-methyl-7H-benzo[c]carbazole-8-carbaldehyde, mp 122°–123.5°, (CH$_2$Cl$_2$/petroleum ether), (C,H,N).

4E.
2-Methyl-2-[[(7H-benzo[c]carbazol-10-yl)methyl]amino]-1,3-propanediol hydrochloride·0.3 H₂O Using the procedure outlined in Example 1, 7-methyl-7H-benzo[c]carbazole-10-carbaldehyde (4B) and 2-amino-2-methyl-1,3-propanediol (Aldrich) gave 2-methyl-2-[[(7-methyl-7H-benzo[c]carbazol-10-yl)methyl]amino]-1,3-propanediol hydrochloride 0.3 H₂O, mp 229°–230° (dec), (C,H,N,Cl), (EtOH/Et₂O).

EXAMPLE 5
2-[[(Benzo[b]naphtho[b]naphtho[2,1-d]furan-5-yl)methyl]amino]-2-methyl-1,3-propanediol

5A. Benzo[b]naphtho[2,1-d]furan-5-carbaldehyde

Benzo[b]naphtho[2,1-d]furan (H. G. Pars Pharmaceutical Laboratories, Inc.) was formylated according to the procedure of A. Rieche et al., *Chem. Ber.* 93, 88 (1960). The crude product appeared to contain only one aldehyde. The crude material was then purified by flush chromatography on SiO₂ with CH₂Cl₂ as the eluting solvent. The appropriate fractions were combined and the solvent removed to give the crude material which was then recrystallized (CH₂Cl₂/hexane) to give a 78% yield of benzo[b]naphtho[2,1-d]furan-5-carbaldehyde, mp 123°–125°, (C,H).

5B. 2-[[(Benzo[b]naphtho[2,1-d]furan-5-yl)methyl]amino]-2-methyl-1,3-propanediol methanesulfonate Using the procedure outlined in Example 1, benzo[b]naphtho(2,1-d]furan-5-carbaldehyde (5A) and 2-amino-2-methyl-1,3-propanediol (Aldrich) gave a 59.2% yield of 2-[[(benzol[b]naphtho[2,1-b]furan-5-yl)methyl]amino]-2-methyl-1,3-propanediol methanisulfonate, mp 216°–218°, (C,H,N,S), (EtOH/Et₂O).

EXAMPLE 6
2-[[(Benzo[b]naphtho[2,3-d]furan-7-yl)methyl]amino]-2-methyl-1,3-propanediol

6A. 7-Bromomethyl-benzo[b]naphtho[2,3-d]furan

To a RB flask was added 7-methyl-benzo[b]naphtho[2,3-d]furan (Cambridge Chemicals, Inc., 16.0 g, 0.07 mol), N-bromosuccinimide (Alsrich 12.8 g, 0.072 mol, recrystallized from H₂O and dried under high vacuum overnight), a catalytic amount of benzoyl peroxide (0.01 g) and CCl₄ (1 L). The mixture was refluxed for 2.5 h, cooled and filtered to remove the succinimide formed in the reaction. The solvent was then removed from the reaction mixture by rotary evaporation. The crude product was purified by flush chromatograhy on SiO₂ using PhCH₃ as the eluting solvent. The appropriate fractions were combined and the solvent once again removed by rotary evaporation to give 22.0 g of product. The material (which was one spot by TLC and pure by NMR) was used without further purification.

6B. 2-[[(Benzo[b]naphtho[2,3-d]furan-7-yl)methyl]amino]-2-methyl-1,3-propanediol methanesulfonate·0.25 H₂O To a RB flask was added 7-bromomethyl-benzo[b]naphtho[2,3-d]furan (6A, 22.0 g, 0.0706 mol), 2-methyl-2-amino-1,3-propanediol (Aldrich, 14.84 g, 0.141 mol), K₂CO₃ (Mallinckrodt, 19.49 g, 0.141 mol) and abs. ethanol (600 mL). The mixture was refluxed overnight, cooled and filtered. The solvent was then removed by rotary evaporation to give a white residue. This was shaken with hot H₂O (500 mL). The mixture was allowed to stand at RT for 1 h and the resulting solid filtered. The mixture was filtered and the resulting solid washed with warm H₂O (2×500 mL). The damp solid was dissolved in abs. EtOH (400 mL) containing methanesulfonic acid (3 mL). The liquid was filtered through a fine fritted flass funnel and the filtrate diluted to 2L with Et₂O. The resulting solid was filtered and recrystallized (EtOH/Et₂O, 1:2). After drying in a vacuum oven overnight at 80°, 9.67 g (32% yield) of 2-[[(benzo[b]naphtho[2,3-d]furan-7-yl)methyl]amino]-2-methyl-1,3-propanediol methanesulfonate·0.25 H₂O, mp 248°–249° (dec), (C,H,N,S).

EXAMPLE 7
2-[[(Benzo[b]naphtho[2,3-d]thiophen-6-yl)methyl]amino]-2-methyl-1,3-propanediol

7A. Benzo[b]naphtho[2,3-d]thiophene-6-carbaldehyde

Beno[b]naphtho[2,3-d]thiophene (Cambridge Chemicals, Inc.) was formylated using the procedure of A. Rieche et al., *Chem Ber* 93, 88 (1960), to give a 78.1% yield of benzo[b]naphtho[2,3-d]thiophene-6-carbaldehyde, mp 199°, (C,H,S), (CH₂Cl₂/hexane).

7B. 2-[[(Benzo[b]naphtho[2,3-d]thiophen-6-yl)methyl]amino]-2-methyl-1,3-propanediol methanesulfonate Using the procedure outlined in Example 1, benzo[b]naphtho[2,3-d]-thiophene-6-carbaldehyde (7A) and 2-amino-2-methyl-1,3-propanediol (Aldrich) gave 67.1% yield of 2-[(benzo[b]naphtho[2,3-d]thiophen-6-yl)-methyl]amino]-2-methyl-1,3-propanediol methanesulfonate, mp 242°–243°, (C,H,N,S), (EtOH/Et₂O).

EXAMPLE 8
2-[[(Benzo[b]naphtho[2,3-d]thiophen-8-yl)methyl]amino]-2-methyl-1,3-propanediol

8A. Benzo[b]naphtho[2,3-d]thiophene-8-carbaldehyde

To a RB flask equipped with magnetic stirring bar, reflux condenser and N₂ inlet line with bubbler was added 2,3-dichloro-5,6-dicyano-1,4-benzoquinone (Aldrich, 38.6 g, 0.119 mol), H₂O (100 mL) and CHCl₃ (1500 mL). After refluxing the mixture for 15 min, 8-methyl-benzo[b]-naphtho[2,3-d]thiophene (Cambridge Chemicals, Inc., 21.0 g, 89.6 mmol) was aded to the flask. After refluxing the mixture for 5 h an additional portion of DDQ (19.3 g, 85 mmol) was added. The mixture was then refluxed overnight, cooled and the deep red solution filtered. The solvent was then removed by rotary evaporation and the residual H₂O removed by azeotropic distillation with several portions of PhCH₃. The material was then dissolved in PhCH₃ (500 mL) and applied to a 40×10 cm column of SiO₂ and eluted with additional PhCH₃ as the solvent. The appropriate fractions were combined and the solvent removed to give 7.12 g of crude material. This was crystallized (PhCH₃), filtered and dried to give 5.35 g (22.7% yield) of benzo[b]naphtho[2,3-d]thiophene-8-carbaldehyde, mp 182°–185°, (C,H,S).

8B. 2-[[(Benzo[b]naphtho[2,3-d]thiophen-8-yl)methyl]amino]-2-methyl-1,3-propanediol methanesulfonate·0.6 H$_2$O Using the procedure outlined in Example 1, benzo[b]naphtho[2,3-d]thiophene-8-carbaldehyde (8A) and 2-amino-2-methyl-1,3-propanediol (Aldrich) gave a 60.1% yield of 2-[[(benzo[b]naphtho[2,3-d]thiophen-8-yl)methyl]-amino]-2-methyl-1,3-propanediol methanesulfonate ·0.6 H$_2$O, mp 245°–246° (dec), (C,H,N,S), (EtOH/Et$_2$O).

EXAMPLE 9

2-[[(Benzo[b]naphtho[2,3-d]thiophen-7-yl)methyl]amino]-2-methyl-1,3-propanediol

9A. Benzo[b]naphtho[2,3-d]thiophene-7-carbaldehyde

Using the procedure described in Example 8, 7-methylbenzo[b]naphtho[2,3-d]thiophene (Cambridge Chemicals, Inc.) gave an 18.7% yield of benzo[b]naphtho[2,3-d]thiophene-7-carbaldehyde, mp 199°–200°, (C,H,S), (PhCH$_3$/hexane).

9B. 2-[[(Benzo[b]naphtho[2,3-d]thiophen-7-yl)methyl]amino]-2-methyl-1,3-propanediol methanesulfonate·0.5 H$_2$O Using the procedure outlined in Example 1, benzo[b]naphtho[2,3-d]thiophene-7-carbaldehyde (9A) and 2-amino-2-methyl-1,3-propanediol (Aldrich) gave 75.8% yield of 2-[[(benzo[b]naphtho[2,3-d]thiophen-b 7-yl)methyl]-amino]-2-methyl-1,3-propanediol methanesulfonate·0.5 H$_2$O, mp 210°–211° (dec), (C,H,N,S), (EtOh/Et$_2$O).

EXAMPLE 10

2-[[(Benzo[b]naphtho[2,3-d]furan-11-yl)methyl]amino]-2-methyl-1,3-propanediol methanesufonate Using the procedure outlined in Example 1, benzo[b]naphtho[2,3-d]furan-11-carbaldehyde (2B) and 2-amino-2-methyl-1,3-propanediol (Aldrich) gave a 68.8% yield of 2-[[(benzo[b]naphtho[2,3-d]furan-11-yl)methyl]amino]-2-methyl-1,3-propanediol methanesuylfonate, mp 219°–220° (dec), (C,H,N,S), (EtOH/Et$_2$O).

EXAMPLE 11

2-[[(5-Ethyl-5H-benzo[b]carbazol-7-yl)methyl]amino]-2-methyl-1,3-propanediol

11A. 5-Ethyl-5H-benzo[b]carbazole-7-carbaldehyde

Using the procedure outlined in Example 8A, 5-ethyl-7-methyl-5H-benzo[b]carbazole (Cambridge Chemicals, Inc.) gave a 15.4% 5-ethyl-5H-benzo[b]carbazole-7-carbaldehyde, mp 130°–133°, (C,H,N), (PhCH$_3$).

11B. 2-[[(5-Ethyl-5H-benzo[b]carbazol-7-yl)methyl]amino]-2-methyl-1,3-propanediol methanesulfonate Using the procedure outlined in Example 1, 5-ethyl-5H-benzo[b]carbazole-7-carbaldehyde (11A) and 2-amino-2-methyl-1,3-propanediol (Aldriche gave 40.2% yield of 2-[[(5-ethyl-5H-benzo[b]carbazol-7-yl)methyl]amino]-2-methyl-1,3-propanediol methanesulfonate, mp 219°–220° (dec), (C,H,N,S), (EtOH/Et$_2$O).

EXAMPLE 12

2-[[(5-Ethyl-5H-benzo[b]carbazol-6-yl)methy]amino]-2-methyl-1,3-propanediol

12A. 5-Ethyl-5H-benzo[b]carbazole-6-carbaldehyde

5-Ethyl-6-methyl-5H-benzo[b]carbazole (Cambridge Chemicals, Inc.) was formylated using the procedure of A. Riche et al., Chem. Ber. 93, 88 (1960) to give a 44.9% yield of 5-ethyl-5H-benzo[b]carbazole-6-carbaldehyde, mp 95.5°–96.5°, (C,H,N), (PhCH$_3$).

12B. 2-[[(5-Ethyl-5H-benzo[b]carbazol-6-yl)methyl]amino]-2-methyl-1,3-propanediol methanesulfonate Using the procedure outlined in Example 1, 5-ethyl-5H-benzo[b]carbazole-6-carbaldehyde (12A) and 2-amino-2-methyl-1,3-propanediol (Aldrich) gave a 68.0% yield of 2-[[(5-ethyl-5H-benzo[b]carbazol-6-yl)methyl]amino]-2-methyl-1,3-propanediol methanesulfonate, mp 174°–175°, (C,H,N,S), (EtOH/Et$_2$O).

EXAMPLE 13

2-[[(Benzo[b]naphtho[1,2-d]thiophen-5-yl)methyl]amino]-2-methyl-1,3-propanediol

13A. Benzo[b]naphtho[1,2-d]thiophene-5-carbaldehyde

Benzo[b]naphtho[1,2-d]thiophene (H. G. Pars Pharmaceutical Laboratories, Inc.) was formylated using the procedure of A. Rieche et al., Chem. Ber. 93, 88 (1960) to give a 49.3% yield of benzo[b]-naphtho[1,2-d]thiophene-5-carbaldehyde, mp 142°–144°, (C,H,S), (CH$_2$Cl$_2$/hexane).

13B. 2-[[(Benzo[b]naphtho[1,2-d]thiophen-5-yl)methyl]amino]-2-methyl-1,3-propanediol methanesulfonate·0.5 H$_2$O Using the procedure outlined in Example 1, benzo[b]naphtho[1,2-d]-thiophen-5-carbaldehyde (13A) and 2-amino-2-2-methyl-1,3-propanediol (Aldrich) gave a 73.7% yield of 2-[[(benzo[b]naphtho[1,2-d]thiophen-5-yl)methyl]amino]-2-methyl-1,3-propanediol methanesulfonate·0.5 H$_2$O, mp 209°–209.5°, (C,H,N,S), (EtOH/Et$_2$O).

EXAMPLE 14

2-Methyl-2-[[(phenanthro[1,2-b]furan-2-yl)methyl]amino]-1,3-propanediol

14A. Phenanthro[1,2-b]furan-2-methanol

To a RB flask equipped with magnetic stirring bar, reflux condenser and N$_2$ inlet tube with bubbler was added ethyl phenanthro[1,2-b]furan-2-carboxylate (H. G. Pars Pharmaceutical Laboratories, Inc., 7.9 g, 27.2 mmol), lithium borohydride (Aldrich, 0.65 g, 30 mmol) and dry THF (400 mL). The mixture was stirred at reflux for 6 h and then poured into H$_2$O (1 L). The reaction mixture was acidified with 1N HCl and the resulting white solid was filtered, washed with additional H$_2$O (1500 mL) then dissolved in CH$_2$Cl$_2$ (500 mL), dried (Na$_2$SO$_4$), filtered, concentrated to 200 mL and diluted to 500 mL with hexane. The resulting material was filtered, washed with hexane (100 mL) and placed in a vacuum oven overnight. A total of 6.1 g (90.1%) of phenanthro[1,2-b]-furan-2-methanol, mp 125°–126° was obtained (C,H).

14B. Phenanthro[1,2-b]furan-2-carbaldehyde

To a RB flask equipped with magnetic stirring bar, reflux condenser, $N_2$ inlet line with bubbler was added phenanthro[1,2-b]furan-2-methanol (14A, 5.84 g, 23.5 mmol), barium manganate (Aldrich, 12.06 g, 47 mmol) and dry $CH_2Cl_2$ (400 mL). The mixture was refluxed for 6 h, filtered and the resulting dark yellow solution filtered through a small plug of $SiO_2$ to remove inorganic salts and polar baseline material. The solvent was then removed by rotary evaporation and the crude material recrystallized using $CH_2Cl_2$/hexane to give after drying 5.17 g (91% yield) of phenanthro[1,2-b]furan-2-carbaldehyde, mp 169°, (C,H).

14C. 2-Methy-2-[(phenanthro[1,2-b]furan-2-yl)methyl]amino]-1,3-propanediol methanesulfonate·0.5 H₂O Using the procedure outlined in Example 1, phenanthro[1,2-b]furan-2-carbaldehyde (14B) and 2-amino-2-methyl-1,3-propanediol (Aldrich) gave a 57.1% yield of 2-methyl-2-[[(phenanthro[1,2-b]furan-2-yl)methyl]amino]-1,3-propanediol methanesulfonate·0.5 H₂O, mp 168°–170° (dec), (C,H,N,S), (EtOH/Et₂O).

EXAMPLE 15

2-Methyl-2-[[(phenanthro[1,2-b]furan-11-yl)methyl]amino]-1,3-propanediol

15A. Ethyl 11-formyl-phenanthro[1,2-b]furan-2-carboxylate

Ethyl phenanthro[1,2-b]furan-2-carboxylate (H. G. Pars Pharmaceutical Laboratories, Inc.) was formylated by the procedure of A. Rieche et al., *CHem. Ber.* 93, 88 (1960) to give a crude mixture of aldehydes in 54% yield which was used in the next step without purification. An analytical sample of the main component of this mixture, ethyl 11-formylphenanthro[1,2-b]furan-2-carboxylate, mp 209°–212° was produced by column chromatography followed by crystallization, (C,H), (CH₂Cl₂/hexane).

15B. Phenanthro[1,2-b]furan-11-carbaldehyde

To a RB flask equipped with magnetic stirring bar, condenser and N₂ inlet line with bubler was added ethyl 11-formyl-phenanthro[1,2-b]-furan-2-carboxylate (15A, 2.5 g, 7.8 mmol), 1N NaOH solution (25 mL), THF (50 mL) and H₂O (25 mL). The mixture was refluxed for 2 h until it became homogeneous. The mixture was acidified with 1N HCl and the solvent removed by rotary evaporation. The crude solid was then heated to 150° with copper powder (0.9 g) and quinoline (Aldrich, 25 mL) for 1 h. The reaction mixture was cooled and the quinoline removed under vacuum to give a crude dark green solid. After chromatography and crystallization (CH₂Cl₂/hexane) 0.71 g (37% yield) OF phenanthro[1,2-b]furan-11-carbaldehyde, mp 145°–150°, (C,H).

15C. 2-Methyl-2[[(phenanthro[1,2-b]furan-11-yl)methyl]amino]-1,3-propanediol methanesulfonate Using the procedure outlined in Example 1, phenanthro[1,2-b]furan-11-carbaldehyde (15B) and 2-amino-2-methyl-1,3-propanediol (Aldrich) gave a 57.6% yield of 2-methyl-2-[[(phenanthro[1,2-b]furan-11-yl)methyl]amino]-1,3-propanediol methanesulfonate, mp 186°–188° (dec), (C,H,N,S), EtOH/Et₂O).

EXAMPLE 16

2-Methyl-2-[[(phenanthro[1,2-b]thiophen-2-yl)methyl]amino]-1,3-propanediol

16A. Phenanthro[1,2-b]thiophene-2-methanol

Using the procedure outlined in 14A, ethyl phenanthro[1,2-b]thiophene-2-carboxylate (H. G. Pars Pharmaceutical Laboratories, Inc.) gave a 98.0% yield of phenanthro[1,2-b]thiophene-2-methanol, mp 169°–170.5° (C,H,S), (CH₂Cl₂/hexane).

16B. Phenanthro[1,2-b]thiophene-2-carbaldehyde

Using the procedure in 14B, phenanthro[1,2-b]thiophene-2-methanol (16A) gave a 82.9% yield of phenanthro[1,2-b]thiophene-2-carbaldehyde, mp 209°–210°, (C,H,S), (CH₂Cl₂/hexane).

16C. 2-Methyl-2-[[(phenanthro[1,2-b]thiophen-2-yl)methyl]amino]-1,3-propanediol methanesulfonate·0.6 H₂O Using the procedure outlined in Example 1, phenanthro[1,2-b]thiophene-2-carbaldehyde (16B) and 2-amino-2-methyl-1,3-propanediol (Aldrich) gave an 82.7% yield of 2-methyl-2-[[(phenanthro[1,2-b]thiophen-2-yl)-methyl]amino]-1,3-propanediol methanesulfonate·0.6 H₂O, mp 209°–209.5° (dec), (C,H,N,S), (CH₃OH/Et₂O).

EXAMPLE 17

2-Methyl-2-[[(phenanthro[1,2-b]thiophen-11-yl)methyl]-amino]-1,3-propanediol

17A. Ethyl 11formylphenanthro[1,2-b]thiophene-2-carboxylate

Ethyl phenanthro[1,2-b]thiophene-2-carboxylate (48.0 g, H. G. Pars Pharmaceutical Laboratories, Inc.) was formylated using the procedure of A. Rieche et al., *Chem. Ber.* 93, 88 (1960) to give a mixture of aldehyde esters. After chromatography on SiO₂ to remove starting material a total of 7.25 g of crude aldehyde esters was obtained. Recrystallization gave 3.96 g (7.6%) of ethyl 11-formylphenanthro-[1,2-b]thiophene-2-carboxylate, mp 196°–197°, (CH₂Cl₂/hexane), (C,H,S).

17B. Phenanthro[1,2-b]thiophene-11-carbaldehyde

Ethyl 11-formyl phenanthro[1,2-b]thiophene-2-carboxylate (17A) was hydrolyzed as in Example 15B and the resulting crude aldehyde acid was decarboxylated as in Example 15B. After chromatography and crystallization, phenanthro[1,2-b]thiophene-11-carbaldehyde, mp 161.5°–162.5° was obtained in 41.2% yield, (C,H,S), (PhCH₃).

17C. 2-Methyl-2-[[(phenanthro[1,2-b]thiophen-11-yl)methyl]amino]-1,3-propanediol methanesulfonate Using the procedure outlined in Example 1, phenanthro[1,2-b]thiophene-11-carbaldehyde (17B) and 2-amino-2-methyl-1,3-propanediol (Aldrich) gave a 56.5% yield of 2-methyl-2-[[(phenanthro[1,2-b]thiophen-11-yl)methyl]amino]-1,3-propanediol methanesulfonate, mp 206°–207° (dec), (C,H,N,S), (EtOH/Et₂O).

EXAMPLE 18

2-Methyl-2-[[(phenanthro[4,3-b]furan-2-yl)methyl]amino]-1,3-propanediol

18A. Phenanthro[4,3-b]furan-2-methanol

Using the procedure outlined in Example 14A, ethyl phenanthro[4,3-b]-furan-2-carboxylate (H. G. Pars Pharmaceutical Laboratories, Inc.) gave a 91% yield of phenanthro[4,3-b]furan-2-methanol, mp 125°–126°, (C,H), (CH$_2$Cl$_2$/hexane).

18B. Phenanthro[4,3-b]furan-2-carbaldehyde

Using the procedure outlined in Example 14B, phenanthro[4,3-b]furan-2-methanol (18A) gave a 91.2% yield of phenanthro[4,3-b]furan-2-carbaldehyde, mp 169°, (C,H), (95% EtOH/Ch$_2$Cl$_2$).

18C. 2-Methyl-2-[[(phenanthro[4,3-b]furan-2-yl)methyl]amino]-1,3-propanediol methanesulfonate Using the procedure outlined in Example 1, phenanthro[4,3-b]furan-2-carbaldehyde (18B) and 2-amino-2-methyl-1,3-propanediol (Aldrich) gave a 56.5% yield of 2-methyl-2-[[(phenanthro[4,3-b]furan-2-yl)methyl]amino]-1,3-propanediol methanesulfonate, mp 186°–188° (dec), (C,H,N,S), (EtOH/Et$_2$O).

EXAMPLE 19

2-Methyl-2-[[(phenanthro[4,3-b]thiophen-7-yl)methyl]amino]-1,3-propanediol

19A. Phenanthro[4,3-b]thiophene-7-carbaldehyde

Using the procedure outlined in Example 17A ethyl phenanthro[4,3-b]-thiophene-2-carboxylate (H. G. Pars Pharmaceutical Laboratories, Inc.) gave a 6.7% yield of phenanthro[4,3-b]thiophen-7-carbaldehyde, mp 173°–177° (C,H,S), (PhCH$_3$).

19B. 2-Methyl-2-[[(phenanthro[4,3-b]thiophen-7-yl)methyl]amino]-1,3-propanediol methanesulfonate·0.25 H$_2$O Using the procedure outlined in Example 1, phenanthro[4,3-b]thiophene-7-carbaldehyde (19A) and 2-amino-2-methyl-1,3-propanediol (Aldrich) gave a 53.8% yield of 2-methyl-2-[[(phenanthro[4,3-b]thiophen-7-yl)-methyl]amino]-1,3-propanediol methanesulfonate·0.25 H$_2$O, mp 189°–191° (dec), (C,H,N,S), (EtOH/Et$_2$O).

EXAMPLE 20

2-Methyl-2-[[(phenanthro[9,10-b]furan-2-yl)methyl]amino]-1,3-propanediol

20A. Phenanthro[9,10-b]furan-2-carbaldehyde

Phenanthro[9,10-b]furan (prepared by the procedure of P. Muller and J. Pfyffer, *Chimia* 38, 79 (1984)) was formylated using the procedure of A. Rieche et al., *Chem. Ber.* 93, 88 (1960) to give a 32.8% yield of phenanthro[9,10-b]furan-2-carbaldehyde, mp 84°–85°, (C,H), (PhCh$_3$).

20B. 2-Methyl-2-[[(phenanthro[9,10-b]furan-2-yl)methyl]amino]-1,3-propanediol methanesulfonate·0.2 H$_2$O·0.2 EtOH Using the procedure outlined in Example 1, phenanthro[9,10-b]furan-2-carbaldehyde (20A) and 2-amino-2-methyl-1,3-propanediol (Aldrich) gave a 39.2% yield of 2-methyl-2-[[(phenanthro[9,10-b]furan-2-yl)methyl]amino]-1,3-propanediol methanesulfonate·0.2 H$_2$O·0.2 EtOH, mp 218°–219° (dec), (C,H,N,S), (EtOH/Et$_2$O).

EXAMPLE 21

2-Methyl-2-[[(phenanthro[9,10-c]thiophen-1-yl)methyl]amino]-1,3-propanediol

21A. Phenanthro[9,10-c]thiophene-1-carbaldehyde

Phenanthro[9,10-c]thiophene (H. G. Pars Pharmaceutical Laboratories, Inc.) was formylated using the procedure of A. Rieche et al., *Chem. Ber.* 93, 88 (1960) to give a 85.9% yield of phenanthro[9,10-c]thiophene-1-carbaldehyde, mp 198°–199°, (C,H,S), (THF/95% EtOH).

21B. 2-Methyl-2-[[(phenanthro[9,10-c]thiophen-1-yl)methyl]amino]-1,3-propanediol methanesulfonate·0.25 H$_2$O Using the procedure outlined in Example 1, phenanthro[9,10-c]thiophene-1-carbaldehyde (21A) and 2-amino-2-methyl-1,3-propanediol (Aldrich) gave a 39.2% yield of 2-methyl-2-[[(phenanthro[9,10-c]thiophen-1-yl)methyl]amino]-1,3-propanediol methanesulfonate·0.25 H$_2$O, mp 180°–187° (dec), (C,H,N,S), (EtOH/Et$_2$O).

EXAMPLE 22

2-[[(Acenadphtho[1,2-b]thiophen-8-yl)methyl]amino]-2-methyl-1,3-propanediol hydrochloride

Using the procedure outlined in Example 1, acenaphtho[1,2-b]thiophene-8-carbaldehyde (H. G. Pars Pharmaceutical Laboratories, Inc.) and 2-amino-2-methyl-1,3-propanediol (Aldrich) gave a 73.8% yield of 2-[[(8-acenaphtho[1,2-b]thiophen-8-yl)methyl]amino]-2-methyl-1,3-propanediol hydrochloride, mp 208°–210° (dec), (C,H,N,Cl,S), (EtOH/Et$_2$O).

EXAMPLE 23

2-[[(Acenaphtho[1,2-c]thiophen-7-yl)methyl]amino]-2-methyl-1,3-propanediol

23A. Acenaphtho[1,2-c]thiophene-7-carbaldehyde

Acenaphtho[1,2-c]thiophene (H. G. Pars Pharmaceutical Laboratories, Inc.) was formylated according to the procedure of A. Riece et al., *Chem Ber.* 93, 88 (1960) to give an 83.2% yield of acenaphtho[1,2-c]-thiophene-7-carbaldehyde, mp 123°–125.5°, (C,H,S).

23B. 2-[[(Aceanphtho[1,2-c]thiophen-7-yl)methyl]amino]-2-methyl-1,3-propanediol hydrochloride Using the procedure outlined in Example 1, acenaphtho[1,2-c]thiophene-7-carbaldehyde (23A) and 2-amino-2-methyl-1,3-propanediol (Aldrich) gave a 57.4% yield of 2-[[(acenaphtho[1,2-c]thiophen-7-yl)methyl]amino]-2-methyl-1,3-propanediol hydrochloride, mp 220°–223° (dec), (C,H,N,Cl,S), (EtOH/Et$_2$O).

Example 24

2-Methyl-2-[[(phenanthro[2,3-b]thiophen-7-yl)methyl]amino]-1,3-propanediol

24A. Phenanthro[2,3-b]thiophen-7-carbaldehyde

Phenanthro[2,3-b]thiophene (H. G. Pars Pharmaceutical Laboratories, Inc. prepared by the procedure of M. Iwao, M. L. Leed and R. N. Castle, *J. Het. Chem.* 17, 1259 (1980) was formylated according to the procedure of A. Rieche et al., *Chem. Ber.* 93, 88 (1960) to give a 58.9% yield of crude aldehydes. After chromatography and crystallization pure phenanthro[2,3-b]-thiophene-7-carbaldehyde, mp 199°-200° (C,H,S) was obtained in 42.7% yield.

24B.
2-Methyl-2-[[(phenanthro[2,3-b]thiophen-7-yl)methyl]amino]-1,3-propanediol methanesulfonate Using the procedure outlined in Example 1, phenanthro[2,3-b]thiophene-7-carbaldehyde (24A) and 2-amino-2-methyl-1,3-propanediol (Aldrich) gave a 71.2% yield of 2-methyl-2-[[(phenanthro[2,3-b]thiophen-7-yl)methyl]amino]-1,3-propanediol methanesulfonate, mp 212°-215° (EtOH/Et$_2$O), (C,H,N,S).

EXAMPLE 25
2-[[(Benzo[b]naphtho[1,2-d]furan-1-yl)methyl]amino]-2-methyl-1,3-propanediol

25A. 1-Bromomethylbenzo[b]naphtho[2,3-d]furan

Using the procedure outlined in 6A, 1-methylbenzo[b]naphtho[2,3-d]furan (Cambridge Chemicals, Inc.) gave 72% yield of crude 1-bromomethylbenzo[b]naphtho[2,3-d]furan which was used without further purification.

25B.
2-[[(Benzo[b]naphtho[1,2-d]furan-1-yl)methyl]amino]-2-methyl-1,3-propanediol methanesulfonate Using the procedure outlined in 6B, 1-bromomethylbenzo[b]naphtho[2,3-d]furan and 2-amino-2-methyl-1,3-propanediol (Aldrich) gave a 36.3% yield of 2-[[(benzo[b]naphtho[1,2-d]furan-1-yl)methyl]amino]-2-methyl-1,3-propanediol methanesulfonate, mp 186°-187° (EtOH/Et$_2$O), (C,H,N,S). EXAMPLE 26

2-Methyl-2-[[(7-methyl-7H-benzo[c]carbazol-8-yl)methyl]amino]-1,3-propanediol hydrochloride Using the procedure outlined in Example 1, 7-methyl-7H-benzo[c]carbazole-8-carbaldehyde gave a 80.7% yield of 2-methyl-2-[[(7-methyl-7H-benzo[c]-carbazol-8-yl)methyl]amino]-1,3-propanediol hydrochloride, mp 260°-261°, CH$_3$OH/Et$_2$O), (C,H,N,Cl).

EXAMPLE 27
2-[[7-Methyl-7H-benzo[c]carbazol-10-yl)methyl]amino]-1,3-propanediol hydrochloride To a RB flask was added 2-amino-1,3-propanediol hydrochloride (Sigma) and an equimolar amount of sodium methoxide (MCB) and CH$_3$OH (100 mL). After warming, the solvent was removed by rotary evaporation, and after addition of 7-methyl-7H-benzo[c]carbazole-10-carbaldehyde (4B), the reaction run following the normal reductive amination procedure outlined in Example 1 to give 2-[[(7-methyl-7H-benzo[c]carbazol-10-yl)methyl]amino]-1,3-propanediol hydrochloride, mp 166°-169°, (abs. EtOH), (C,H,N,Cl).

EXAMPLE 28
(1S,2S)-2-[[(7-Methyl-7H-benzo[c]carbazol-10-yl)methyl]amino]-1-phenyl-1,3-propanediol hydrochloride To a RB flask was added (+)-1S,2S-2-amino-1-phenyl-1,3-propanediol hydrochloride (Aldrich) and an equimolar amount of sodium methoxide (MCB) and CH$_3$OH (100 mL). After warming, the solvent was removed by rotary evaporation, and after addition of 7-methyl-7H-benzo[c]carbazole-10-carbaldehyde (4B), the reaction run following the normal reductive amination procedure outlined in Example 1 to give 21.3% yield of (1S,2S)-2-[[(7-methyl-7H-benzo[c]carbazol-10-yl)methyl]amino]-1-phenyl-1,3-propanediol hydrochloride, mp 220°-221.5°, (EtOH/Et$_2$O), (C,H,N,Cl).

EXAMPLE 29
2-Ethoxymethyl-2-[[(7-methyl-7H-benzo[c]carbazol-10-yl)methyl]-amino]-1,3-propanediol

29A.
3,5-Diphenyl-7a(7H)-ethoxymethyl-1H,3H,5H-oxazolo[3,4-c[oxazole

A mechanically stirred 60% dispersion of NaH in mineral oil (Alfa, 34.0 g, 0.85 mol) was washed with dry hexane to remove the oil and suspended to dry DMF (300 mL). To the mixture was added a solution of 3,5-diphenyl-1H,3H,5H-oxazolo[3,4-c]oxazole-7a(7H)-methanol (208.2 g, 0.7 mol, prepared by the method of J. Pierce et al., *J. Amer. Chem. Soc.* 73, 2595 (1951)) in dry DMF (300 mL) keeping the reaction mixture between 30°-35°. The salt suspension was stirred at RT for 60 min, diluted with dry DMF (200 mL) to facilitate stirring, cooled, then treated with ethyl iodide (Aldrich, excess) at such a rate that the reaction temperature was between 20°-35°. The mixture was stirred at RT for 2 h, then cautiously treated with abs. EtOH (30 mL). The resulting mixture was diluted with Et$_2$O (2.5 L) and the resulting solids removed by filtration. The solvent was then removed using a rotary evaporator to give 229.5 g of a yellow oil containing both starting material and desired product. A solution of the oil in chloroform was mixed with SiO$_2$ (200 g) and the solvent removed. The solid was then added to a column of SiO$_2$ (800 g). Elution with the EtOAc/hexane (1:3.5) gave 139.7 g (61.3%) of 3,5-diphenyl-7a(7H)-ethoxymethyl-1H,3H,5H-oxazolo[3,4-c]oxazole. An analytical sample was obtained by recrystallization from hexane, mp 83.5°-85°, (C,H,N). The bulk of the material was used without further purification.

29B. 2-Amino-2-ethyoxymethyl-1,3-propanediol hydrochloride·¼ H$_2$O 3,5-Diphenyl-7a(7H)-ethoxymethyl-1H,3H,5H-oxazolo(3,4-c)oxazole (29A, 136 g, 0.42 mol) was dissolved in 6N HCl (400 mL) and the resulting solution stirred 1.5 h at RT. After extraction with Et$_2$O (2×200 mL) to remove benzaldehye, the aqueous solution was concentrated on a rotary evaporator to give a colorless oil. This was cooled in an ice bath to facilitate cyrstallization. The solid which formed was slurried with cold CH$_3$CN, filtered, then washed with Et$_2$O and dried in a vacuum oven at RT to give 71 g (89%) of 2-amino-2-ethoxymethyl-1,3-propanediol hydrochloride·¼ H$_2$O mp 78°-79°, (C,H,Cl,S).

29C.
2-Ethoxymethyl-2-[[(7-methyl-7H-benzo[c]carbazol-10-yl)methyl]amino]-1,3-propanediol hydrochloride To a RB flask was added 2-amino-2-ethoxymethyl-1,3-propanediol hydrochloride·¼ H$_2$O (29B) and an equimolar amount of sodium methoxide (MCB) and CH$_3$OH (100 mL). After warming, the solvent was removed by rotary evaporation, and after addition of 7-methyl-7H-benzo[c]carbazole-10-carbaldehyde (4B), the reaction run following the normal reductive amination procedure outlined in Example 1 to give a 23.5% yield of 2-ethoxymethyl-2-[[(7-methyl-7H-benzo[c]carbazol-10-yl)methyl]amino]-1,3-propanediol hydrochloride, mp 185°–186°, (i-PrOH/Et₂O), (C,H,Cl,N).

EXAMPLE 30

2-Ethyl-2-[[(7-methyl-7H-benzo[c]carbazol-10-yl)methyl]amino]-1,3-propanediol hydrochloride Using the procedure outlined in Example 1, 7-methyl-7H-benzo[c]carbazole-10-carbaldehyde (4B) and 2-amino-2-ethyl-propanediol (Aldrich) gave a 38.6% yield of 2-ethyl-2-[[(7-methyl-7H-benzo[c]carbazol-10-yl)methyl]amino]-1,3-propanediol hydrochloride, mp 188.5°–190° (abs. EtOH), (C,H,N,Cl).

EXAMPLE 31

2-[[(7-Methyl-7H-benzo[c]carbazol-10-yl)methyl]amino]-2-methyl-1-propanol hydrochloride·0.20 H₂O Using the procedure outlined in Example 1, 7-methyl-7H-benzo[c]carbazole-10-carbaldehyde (4B) and 2-amino-2-methyl-1-propanol (Aldrich) gave a 72.4% yield of 2-[[(7-methyl-7H-benzo[c]carbazol-10-yl)methyl]amino]-2-methyl-1-propanol hydrochloride·0.20 H₂O, mp 219°–220° (abs. EtOH), (C,H,N,Cl).

EXAMPLE 32

(±)-(2R*,3S*)-2-Methyl-2-[[(7-methyl-7H-benzo[c]carbazol-10-yl)methyl]amino]-1,3-butanediol 32A. (±)-(2R*,3S*)-2-Methyl-2-nitro-1,3-butanediol
and
32B. (±)-(2R*,3R*)-2-Methyl-2-nitro-1,3-butanediol To a mixture of 2-nitro-1-propanol (Aldrich, 63.0 g, 0.60 mol) and acetaldehyde (Eastman, 39.6 g, 0.90 mol) cooled in an ice bath under N₂ was added cold H₂O (40 mL) and calcium hydroxide (200 mg). The mixture was allowed to warm to RT over 2 h and then stirred for 68 h. The resulting solution was neutralized with excess solid CO₂. The mixture was stirred for 1 h before filtration through a Millipore ® filter. The filtrate was then concentrated under vacuum at 35°. The residue, a viscous syrup partially crystallized on drying under vacuum (0.1 mm, RT, 48 h) was then triturated with cold Et₂O (35 mL). The white crystals which formed were collected by filtration, washed with cold Et₂O (3 × 15 mL) and dried under vacuum (0.1 mm, RT) to give 34.1 g of material, judged by NMR to be (±)-(2R*,3S*)-2-methyl-2-nitro-1,3-butanediol (32A) (purity >97%, racemic). After recrystallization, the diastereomeric purity was >99%, mp 78.5°–81° (lit. 78°; cf. Beil 1, 482, in Henry, Bull. Soc. Chim. Fr. [3] 15, 1224), (C,H,N).

The original filtrate (including washes) was concentrated under vacuum to a pale yellow liquid which was subjected to flash chromatography as follows: The sample was mixed with hexane/EtOAc (2:1, 100 mL) and added to a column of dry SiO₂ (1.5 kg). The column was eluted with hexane/EtOAc (2:1, 12 L) then hexane/EtOAc (1:1, 6 L) while 500 mL fractions were collected. Appropriate fractions were combined. Pure product was found in the final 8 L which, after concentration, gave 38.7 g of viscous syrup, judged by NMR to be a 1:1 mixture of the two racemic diastereomers (32A and 32B), (C,H,N).

This and another batch of the 1:1 diasteriomeric mixture of 32A and 32B (prepared as described above) were combined (67 g, total) and subjected to successive liquid-liquid partitioning between H₂O and EtOAc to give pure samples (99% on the basis of NMR and HPLC (Hamilton PRP-1 column using 3.5% aqueous acetonitrile as the mobile phase) of (±)-(2R*,3S*)-2-methyl-2-nitro-1,3-butanediol (32A) (24.9 g, k'=4.3, mp 79°–81°, C,H,N) and (±)-(2R*,3R*)-2-methyl-2-nitro-1,3-butanediol (32B) (15.8 g, k'=2.1, C,H,N a colorless, viscous liquid).

32C.
(±)-(2R*,4S*,5R*)-4,5-dimethyl-5-nitro-2-phenyl-1,3-dioxane and 32D.
(±)-(2R*,4S*,5S*)-4,5-dimethyl-5-nitro-2-phenyl-1,3-dioxane The relative configurations of the two diasteriomeric pairs (32A and 32B) were unequivocally assigned on the basis of comparative NMR analysis of the respective cyclic acetals derived from benzaldehyde. Thus, 32A (1.49 g, 0.01 mol) and benzaldehyde (Mallinckrodt, 1.06 g, 0.01 mol) were condensed in benzene in the presence of a catalytic amount of p-toluenesulfonic acid (Fisher) with azeotropic removal of water (according to the method of H. Piotrowska, B. Serafin and T. Urbanski, Tetrahedron 109, 379 (1963)). After successive washing with saturated NaHCO₃ solution, drying (MgSO₄), filtration, and removal of the benzene by rotary evaporation, a pale yellow solid was obtained. A solution of this product is ethanol at 0° provided an oil which was isolated by decanting the mother liquor and drying under vacuum (0.1 mm, RT). The yield was 1.48 g (62%) of (±)-(2R*,4S*,5R*)-4,5-dimethyl-5-nitro-2-phenyl-1,3-dioxane (32C) (C,H,N).

Similarly prepared from 32B and benzaldehyde was (±)-(2R*,4S*,5S*)-4,5-dimethyl-5-nitro-2-phenyl-1,3-dioxane (32D) (74%) (C,H,N).

32E. (±)-(2R*,3R*)-2-Amino-2-methyl-1,3-butanediol acetate

To a solution of (±)-(2R*,3R*)-2-methyl-2-nitro-1,3-butanediol (32B, 13.93 g, 0.093 mol) in 95% EtOH (120 mL) was added glacial acetic acid (17 mL) and 10% Pd/C (MCB, 1.0 g). The mixture was reduced in a Parr apparatus at 50 psi of H₂ for 48 h. The catalyst was then removed by filtration on a Celite ® pad and the solvent removed to give the crude amine salt. Three portions of PhCH₃ (50 mL) were added to the flask and removed by rotary evaporation to remove final traces of H₂O and acetic acid. The residue, a viscous oil gradually solidified under high vacuum. The solie was triturated with Et₂O, filtered and the resulting solid further washed with Et₂O to give after drying, 16.23 g (97%) of (±)-(2R*,3R*)-2-amino-2-methyl-1,3-butanediol acetate, mp 117°–121°, (C,H,N).

32F. (±)-(2R*,3S*)-2-Amino-2-methyl-1,3-butanediol acetate

Using the procedure described for 32E, (±)-(2R*,3S*)-2-methyl-2-nitro-1,3-butanediol (32A, 41.1 g, 0.276 mol) gave 46.12 g (93.5%) of (±)-(2R*,3S*)-2-amino-2-methyl-1,3-butanediol acetate, mp 163°–165°, (C,H,N).

32G.
(±)-(2R*,3S*)-2-Methyl-7H-benzo[c]carbazol-10-yl)methyl]amino]-1,3-butanediol hydrochloride·0.2 H₂O To a RB flask was added (±)-(2R*,3S*)-2-amino-2-methyl-1,3-butanediol acetate (32F), an equimolar amount of sodium methoxide (MCB) and CH₃OH (100 mL). After warming, the solvent was removed by rotary evaporation, and after addition of 7-methyl-7H-benzo[c]carbazole-10-carbaldehyde (4B), the reaction run following the normal reductive amination procedure outlined in Example 1 to give a 21.3% yield of (±)-(2R*,3S*)-2-methyl-2-[[(7-methyl-7H-benzo[c]carbazol-10-yl)methyl]amino]-1,3-butanediol hydrochloride·0.2 H$_2$O, mp 215°-216°, (EtOH/Et$_2$O), (C,H,N,Cl).

EXAMPLE 33

2-Methyl-2-[[(7-methyl-7H-benzo[c]carbazol-5-yl)methyl]amino]-1,3-propanediol hydrochloride Using the procedure outlined in Example 1, 7-methyl-7H-benzo[c]carbazole-5-carbaldehyde (4C) and 2-amino-2-methyl-1,3-propanediol (Aldrich) gave a 72.9% yield of 2-methyl-2-[[(7-methyl-7H-benzo[c]carbazol-5-yl)methyl]amino]-1,3-propanediol hydrochloride, mp 235°-236° (CH$_3$Oh/Et$_2$O), (C,H,N,Cl).

EXAMPLE 34

2-[[(7-EThyl-7H-benzo[c]carbazol-10-yl)methyl]amino]-2-methyl-1,3-propanediol

34A. 7-Ethyl-10-methyl-7H-benzo[c]carbazole

To a RB flask equipped with magnetic stirring bar, reflux condenser, rubber septum and N$_2$ inlet line was added a 50% oil dispersion of NaH (7.47 g, 0.155 mol). The oil was removed by washing the dispersion with hexane (3×φmL). Dry THF (100 mL) was added to the flask by cannula to cover the NaH. A solution of 10-methyl-7H-benzo[c]carbazole (Cambridge Chemicals, Inc., 30.0 g, 0.113 mol) in THF (250 mL) was added to the flask by cannula. The mixture was stirred for 30 min at RT. Diethyl sulfate (Aldrich, 24.1 g, 0.156 mol, 20.4 mL) was then added to the flask by syringe and the resulting mixture stirred overnight at RT. H$_2$O (20 mL) was added to the flask to destroy excess NaH. The mixture was then extracted with CH$_2$Cl$_2$ (3×1 L). The organic layers were combined and washed sequentially with H$_2$O (3×500 mL), saturated NaCl solution (3×500 mL), dried (Na$_2$SO$_4$) and concentrated to give a 38.7 g of a crude oil. This material was passed through a plug of Magnesol ® using CH$_2$Cl$_2$ as the eluting solvent. The appropriate fractions were combined and the solvent removed to give after drying 34.1 g of a crude oil. This material was recrystallized from CH$_3$OH to give 28.3 g (84.0) of 7-ethyl-10-methyl-7H-benzo[c]carbazole, mp 69°-74°, (C,H,N).

34B. 7-Ethyl-7H-benzo[c]carbazole-10-carbaldehyde

Using the procedure outlined in Example 8A, 7-ethyl-10-methyl-7H-benzo[c]carbazole (34A) gave a 55.4% yield of 7-ethyl-7H-benzo[c]carbazole-10-carbaldehyde, mp 143°-144°, (CH$_2$Cl$_2$/hexane), (C,H,N).

34C. 2-[[(7-Ethyl-7H-benzo[c]carbazol-10-yl)methyl]amino]-2-methyl-1,3-propanediol hydrochloride Using the procedure outlined in Example 1, 7-ethyl-7H-benzo[c]carbazole-10-carbaldehyde (34B) and 2-amino-2-methyl-1,3-propanediol (Aldriche gave a 77.8% yield of 2-[[(7-ethyl-7H-benzo[c]carbazol-10-yl)methyl]amino]-2-methyl-1,3-propanediol hydrochloride, mp 159°-162° (EtOH/Et$_2$O), (C,H,N,Cl).

EXAMPLE 35

(±)-(2R*,3S*)-2-[(7-Ethyl-7H-benzo[c]carbazol-10-yl)methyl]amino]-2-methyl-1,3-butanediol hydrochloride To a RB flask was added (±)-(2R*,3S*)-2amino-2-methyl-1,3-butanediol acetate (32F), an equimolar amount of sodium methoxide (MCB) and CH$_3$OH (100 mL). After warming, the solvent was removed by rotary evaporation, and after addition of 7-ethyl-7H-benzo[c]carbazole-10-carbaldehyde (34B), the reaction run following the normal reductive amination procedure outlined in Example 1 to give a 23.6% yield of (±)-(2R*,3S*)-2-[(7-ethyl-7H-benzo[c]-carbazol-10-yl)methyl]amino]-2-methyl-1,3-butanediol hydrochloride, mp 209.5°-211°, (EtOh/Et$_2$O), (C,H,N,Cl).

EXAMPLE 36

2-[[(7-Ethyl-7H-benzo[c]carbazol-9-yl)methyl]amino]-2-methyl-1,3-propanediol

36A. 9-Methyl-7H-benzo[c]carbazole

A crude mixture of 9-methyl-7H-benzo[c]carbazole and 11-methyl-7H-benzo[c]carbazole (Camdbridge Chemicals, Inc., 383 g) consisting of an oil with solid in it was filtered. The remaining solid was washed with cold hexane and dried to give 93 g of brown crystals. This was crystallized twice from CH$_3$OH, dissolved in PhCH$_3$ and passed through a plug of Magnesol ® using PhCH$_3$ as the eluting solvent. The appropriate fractions were combined and the solvent removed to give 81 g of white crystals which were shown by NMR to be 9-methyl-7H-benzo[c]carbazole. 0.20 H$_2$O, mp 135°-136° (C,H,N). The oil that was removed by filtration (290 g) was shown by NMR to be a ~1:1 ratio of 9-methyl-7H-benzo[c]carbazole and 11-methyl-7H-benzo[c]carbazole which was used in the next step.

36B. 9-Methyl-7H-benzo[c]carbazole and 11-Methyl-7H-benzo[c]carbazole

The mixture of 9-methyl-7H-benzo[c]carbazole and 11-methyl-7H-benzo[c]carbazole from 36A (290 g) was dissolved in PhCH$_3$ and chromatographed on a plug of Magnesol ® 3X using PhCH$_3$ as the eluting solvent to give 164 g of a dark yellow oil. This was extracted with hot hexane (10×1 L). The fractions were combined and allowed to cool to RT and then refrigerated overnight. The white solid which formed was filtered, washed with hexane (2 L) and dried in a vacuum oven to give 62 g of material which was shown by NMR to be a mixture of 11-methyl-7H-benzo[c]carbazole and 9-methyl-7H-benzo[c]carbazole in a 1.5:1 ratio respectively, mp 101°-127°, (C,H,N).

36C. 7-Ethyl-9-methyl-7H-benzo[c]carbazole

Using the procedure outlined in Example 34A, 9-methyl-7H-benzo[c]carbazole (36A) gave a 98.1% yield of crude 7-ethyl-9-methyl-7H-benzo[c]carbazole which was used without further purification. An analytical sample was recrystallized from hexane, mp 123°-124°, (C,H,N).

36D. 7-Ethyl-7H-benzo[c]carbazole-9-carbaldehyde

Using the procedure outlined in Example 8A, 7-ethyl-9-methyl-7H-benzo[c]carbazole gave a 28.1% yield of 7-ethyl-7H-benzo[c]carbazole-9-carbaldehyde, mp 148.5°-149°, (CH$_2$Cl$_2$), (C,H,N).

36E.
2-[[(7-Ethyl-7H-benzo[c]carbazol-9-yl)methyl]amino]-2-methyl-1,3-propanediol hydrochloride·0.40 H₂O Using the procedure outlined in Example 1, 7-ethyl-7H-benzo[c]carbazole-9-carbaldehyde (36D) and 2-amino-2-methyl-1,3-propanediol (Aldrich) gave a 40.8% yield of 2-[[(7-ethyl-7H-benzo[c]carbazol-9-yl)methyl]amino]-2-methyl-3-propanediol hydrochloride·0.40 H₂O, mp 247°-248°, (EtOH/Et₂O), (C,H,N,Cl).

EXAMPLE 37

2-[[(7-Ethyl-7H-benzo[c]carbazol-11-yl)methyl]amino]-2-methyl-1,3-propanediol

37A. 7-Ethyl-7H-benzo[c]carbazole-11-carbaldehyde

Using the procedure outlined in Example 34A, the mixture of 9-methyl-7H-benzo[c]carbazole and 11-methyl-7H-benzo[c]carbazole (36B) gave a 93.9% crude yield of a mixture of 7-ethyl-9-methyl-7H-benzo[c]carbazole and 7-ethyl-11-methyl-7H-benzo[c]carbazole which was used without further purification. Using the procedure outlined in Example 8A, this mixture gave a mixture of 7-ethyl-7H-benzo[c]carbazole-9-carbaldehyde and 7-ethyl-7H-benzo[c]carbazole-11-carbaldehyde which was separated by chromatography. Pure 7-ethyl-7H-benzo[c]carbzole-11-carbaldehyde was obtained in 21.6% yield (from the mixture), mp 90.5°-91.5° (CH₂Cl₂), (C,H,N).

37B.
2-[[(7-Ethyl-7H-benzo[c]carbazol-11-yl)methyl]amino]-2-methyl-1,3-propanediol hydrochloride·0.40 H₂O·0.50 i-PrOH Using the procedure outlined in Example 1, 7-ethyl-7H-benzo[c]carbazole-11-carbaldehyde (37A) and 2-amino-2-methyl-1,3-propanediol (Aldrich) gave a 15.3% yield of 2-[[(7-ethyl-7H-benzo[c]carbazol-11-yl)methyl]amino]-2-methyl-1,3-propanediol hydrochloride·0.40 H₂O·0.50 i-PrOH, mp 247°-248°, (EtOH/Et₂O), (C,H,N,Cl).

EXAMPLE 38

2-[[(7-Ethyl-7H-benzo[c]carbazol-8-yl)methyl]amino]-2-methyl-1,3-propanediol

38A. 7-Ethyl-8-methyl-7H-benzo[c]carbazole

Using the procedure outlined in Example 34A, 8-methyl-7H-benzo[c]carbazole (Cambridge Chemicals, Inc.) gave a 79.1% yield of 7-ethyl-8-methyl-7H-benzo[c]carbazole, mp 79°-83°, (hexane), (C,H,N).

38B. 7-Ethyl-7H-benzo[c]carbazole-8-carbaldehyde

Using the procedure outlined in 8A, 7-ethyl-8-methyl-7H-benzo[c]carbazole gave a 17.2% of 7-ethyl-7H-benzo[c]carbazole-8-carbaldehyde, mp 148°-149°, (CH₂Cl₂/hexane), (C,H,N).

38C.
2-[[(7-Ethyl-7H-benzo[c]carbazol-8-yl)methyl]amino]-2-methyl-1,3-propanediol hydrochloride Using the procedure outlined in Example 1, 7-ethyl-7H-benzo[c]carbazole-8-carbaldehyde gave a 45.3% yield of 2-[[(7-ethyl-7H-benzo[c]carbazol-8-yl)methyl]amino]-2-methyl-1,3-propanediol hydrochloride, mp 202°-203°, (i-PrOH/Et₂O), (C,H,N,Cl).

EXAMPLE 39

2-Methyl-2-[[(11-methyl-11H-benzo[a]carbazol-5-yl)methyl]amino]-1,3-propanediol

39A. 11-Methyl-11H-benzo[a]carbazole

Using the procedure outlined in Example 34A, 11H-benzo[a]carbazole (Cambridge Chemicals, Inc.) gave a 97.3% yield of 11-methyl-11H-benzo[a]carbazole, mp 167°-169°, (hexane), (C,H,N).

39B.
11-Methyl-11H-benzo[a]carbazole-5-carbaldehyde·0.06 H₂O

11-Methyl-11H-benzo[a]carbazole (39B) was formylated according to the procedure of A. Rieche et al., *Chem. Ber.* 93, 88 (1960) to give a 51.0% yield of 11-methyl-11H-benzo[a]carbazole-5-carbaldehyde·0.06 H₂O, mp 188°-192°, (CH₂Cl₂), (C,H,N).

39C.
2-Methyl-2-[[(11-methyl-11H-benzo[a]carbazol-5-yl)methyl]amino]-1,3-propanediol hydrochloride·0.5 H₂O Using the procedure outlined in Example 1, 11-methyl-11H-benzo[a]carbazole-5-carbaldehyde and 2-amino-2-methyl-1,3-propanediol (Aldrich) gave an 18.1% yield of 2-methyl-2-[[(11-methyl-11H-benzo[a]carbazol-5-yl)methyl]amino]-1,3-propanediol hydrochloride·0.5 H₂O, mp 186°-187°, (EtOH/Et₂O), (C,H,N,Cl).

EXAMPLE 40

(±)-(2R*,3S*)-2-Methyl-2-[[(11-methyl-11H-benzo[a]carbazol-5-yl)methyl]amino]-1,3-butanediol To a RB flask was added (±)-(2R*,3S*)-2-amino-2-methyl-1,3-butanediol acetate (32F), an equimolar amount of sodium methoxide (MCB) and CH₃OH (100 mL). After warming, the solvent was removed by rotary evaporation, and after addition of 11-methyl-11H-benzo[a]carbazole-5-carbaldehyde (39B), the reaction run following the normal reductive amination procedure outlined in Example 1 to give a 49.9% yield of (±)-(2R*,3S*)-2-methyl-2-[[(11-methyl-11H-benzo[a]carbazol-5-yl)methyl]amino]-1,3-butanediol hydrochloride·0.10 H₂O·0.15 EtOH, mp 188°-190°, (EtOH/Et₂O), (C,H,N,Cl).

EXAMPLE 41

2-[[(11-Ethyl-11Hbenzo[a]carbazol-8-yl)methyl]amino]-2-methyl-1,3-propanediol

41A. 11-Ethyl-8-methyl-11H-benzo[a]carbazole

Using the procedure outlined in 34A, 8-methyl-11H-benzo[a]carbazole gave a 76.2% yield of 11-ethyl-8-methyl-11H-benzo[a]carbazole, mp 111°-114°, (CH₂Cl₂/petroleum ether), (C,H,N).

41B. 11-Ethyl-11H-benzo[a]carbazole-8-carbaldehyde

Using the procedure outlined in Example 8A, 11-ethyl-8-methyl-11H-benzo[a]carbazole gave a 26.6% yield of 11-ethyl-11H-benzo[a]carbazole-8-carbaldehyde·0.12 H₂O, mp 135°-139.5°, (CH₂Cl₂/petroleum ether), (C,H,N).

41C.
2-[[(11-Ethyl-11H-benzo[a]carbazol-8-yl)methyl]amino]-2-methyl-1,3-propanediol hydrochloride Using the procedure outlined in Example 1, 11-ethyl-11H-benzo[a]carbazole-8-carbaldehyde (41B) and 2-amino-2-methyl-1,3-propanediol (Aldrich) gave a 69.1% yield of 2-[[(11-ethyl-11H-benzo[a]carbazol-8-yl)methyl]amino]-2-methyl-1,3-propanediol hydrochloride, mp 254°–256°, (CH$_3$OH/Et$_2$O), (C,H,N,Cl).

EXAMPLE 42

2-[[(11-Ethyl-11H-benzo[a]carbazol-9-yl)methyl]amino]-2-methyl-1,3-propanediol

42A. 11-Ethyl-9-methyl-11H-benzo[a]carbazole

Using the procedure outlined in Example 34A, 9-methyl-11H-benzo[a]carbazole (Cambridge Chemicals, Inc.) gave an 84.0% yield of 11-ethyl-9-methyl-11H-benzo[a]carbazole, mp 103.5°–105°, (CH$_3$OH), (C,H,N).

42B. 11-Ethyl-11H-benzo[a]carbazole-9-carbaldehyde

Using the procedure outlined in Example 8A, 11-ethyl-9-methyl-11H-benzo[a]carbazole (42A) gave a 7.5% yield of 11-ethyl-11H-benzo[a]carbazole-9-carbaldehyde, mp 138°–139°, (CH$_2$Cl$_2$/hexane), (C,H,N).

42C.
2-[[(11-Ethyl-11H-benzo[a]carbazol-9-yl)methyl]amino]-2-methyl-1,3-propanediol hydrochloride·0.3 EtOH Using the procedure outlined in Example 1, 11-ethyl-11H-benzo[a]carbazole-9-carbaldehyde (42B) and 2-amino-2-methyl-1,3-propanediol (Aldrich) gave a 48.6% yield of 2[[(11-ethyl-11H-benzo[a]carbazol-9-yl)methyl]amino]-2-methyl-1,3-propanediol hydrochloride·0.3 EtOH, mp 233°–234.5° (dec), (EtOH/Et$_2$O), (C,H,N,Cl).

EXAMPLE 43

2-[[(Benzo[b]naphtho[1,2-d]furan-10-yl)methyl]amino]-2-methyl-1,3-propanediol

43A. 10-Bromomethyl-benzo[b]naphtho[1,2-d]furan

Using the procedure outlined in Example 6A, 10-methyl-benzo[b]naphtho[1,2-d]furan (Cambridge Chemicals, Inc.), gave a nearly quantitative yield of 10-bromomethyl-benzo[b]naphtho[1,2-d]furan which was used without further purification in the next step.

43B.
2-[[(Benzo[b]naphtho[1,2-d]furan-10-yl)methyl]amino]-2-methyl-1,3-propanediol methanesulfonate Using the procedure outlined Example 6B, 10-bromomethylbenzo[b]naphtho[1,2-d]furan (43A) and 2-amino-2-methyl-1,3-propanediol (Aldrich) gave a 33.3% yield of 2-[[(benzo[b]naphtho[1,2-d]furan-10-yl)methyl]amino]2-methyl-1,3-propanediol methanesulfonate, mp 193°–196° (EtOH/Et$_2$O), (C,H,N,S).

EXAMPLE 44

2-Methyl-2-[[(phenanthro[1,2-b]thiophen-5-yl)methyl]amino]-1,3-propanediol

44A. 5-Methylphenanthro[1,2-b]thiophene

Ethyl 5-methylphenanthro[1,2-b]thiophene-2-carboxylate (H. G. Pars Pharmaceutical Laboratories, Inc.) was hydrolyzed and decarboxylated according to the procedure outlined in Example 15B to give an 82.3% yield of 5-methylphenanthro[1,2-b]thiophene, mp 129.5°–131°, (EtOH), (C,N,S).

44B. Phenanthro[1,2-b]thiophene-5-carbaldehyde

Using the procedure outlined in Example 8A, 5-methylphenanthro[1,2-b]thiophene (44A) gave a 17.4% yield of 5-methylphenanthro[1,2-b]thiophene-5-carbaldehyde, mp 174°–175°, (CH$_2$Cl$_2$/hexane), (C,H,S).

44C.
2-Methyl-2-[[(phenanthro[1,2-b]thiophen-5-yl)methyl]amino]-1,3-propanediol methanesulfonate·0.6 H$_2$O Using the procedure outlined in Example 1, phenanthro[1,2-b]thiophene-5-carbaldehyde (44B) and 2-amino-2-methyl-1,3-propanediol (Aldrich) gave a 54.2% yield of 2-methyl-2-[[(phenanthro[1,2-b]thiophen-5-yl)methyl]amino]-1,3-propanediol methanesulfonate·0.6 H$_2$O), mp 215.5°–216°, (EtOH/Et$_2$O), (C,H,N,S).

EXAMPLE 45

2-Methyl-2-[[(phenanthro[1,2-b]furan-5-yl)methyl]amino]-1,3-propanediol

45A. 5-Methylphenanthro[1,2-b]furan

Ethyl 5-methylphenanthro[1,2-b]furan-2-carboxylate (H. G. Pars Pharmaceutical Laboratories, Inc.) was hydrolyzed and decarboxylated according to the procedure outlined in Example 15B to give a nearly quantitative yield of 5-methylphenanthro[1,2-b]furan which was used in the next step without further purification.

45B. Phenanthro[1,2-b]furan-5-carbaldehyde

Using the procedure outlined in Example 8A, 5-methylphenanthro[1,2-b]furan (45A) gave a 30.6% yield of phenanthro[1,2-b]furan-5-carbaldehyde, mp 164°–166°, (PhCH$_3$/hexane), (C,H).

45C.
2-Methyl-2-[[(phenanthro[1,2-b]furan-5-yl)methyl]amino]-1,3-propanediol methanesulfonate Using the procedure outlined in Example 1, phenanthro[1,2-b]furan-5-carbaldehyde (45B) and 2-amino-2-methyl-1,3-propanediol (Aldrich) gave a 59.6% yield of 2-methyl-2-[[(phenanthro[1,2-b]furan-5-yl)methyl]amino]-1,3-propanediol methanesulfonate, mp 193°–193.5°, (EtOH/Et$_2$O), (C,H,N,S).

EXAMPLE 46

(±)-(2R*,3S*)-2-[[(Benzo[b]naphtho[2,3-d]furan-6-yl)methyl]amino]-2-methyl-1,3-butanediol To a RB flask was added (±)-(2R*,3S*)-2-amino-2-methyl-1,3-butanediol acetate (32F), an equimolar amount of sodium methoxide (MCB) and CH$_3$OH (100 mL). After warming, the solvent was removed by rotary evaporation, and after addition of benzo[b]naphtho[2,3-d]furan-6-carbaldehyde (2A), the reaction run following the normal reductive amination procedure outlined in Example 1 to give a 19.6% yield of (±)-(2R*,3S*)-2-[[(benzo[b]naphtho[2,3-d]furan-6-yl)methyl]amino]-2-methyl-1,3-butanediol hydrochloride, mp 206.5°–208°, (abs. EtOH), (C,H,N,Cl).

EXAMPLE 47

2-Methyl-2-[[(phenanthro[3,2-b]thiophen-7-yl)methyl]amino]-1,3-propanediol

47A. Phenanthro[3,2-b]thiophene-7-carbaldehyde

Phenanthro[3,2-b]thiophene (H. G. Pars Pharmaceutical Laboratories, Inc.) was formylated according to the procedure of A. Rieche et al., Chem. Ber. 93, 88 (1960) to give a 70.5% yield of phenanthro[3,2-b]thiophene-7-carbaldehyde, mp 178.5°–180°, (CH$_2$Cl$_2$), (C,H,S).

47B. 2-Methyl-2-[[(phenanthro[3,2-b]thiophen-7-yl)methyl]amino]-1,3-propanediol methanesulfonate Using the procedure outline in Example 1, phenanthro[3,2-b]thiophene-7-carbaldehyde (47A) and 2-amino-2-methyl-1,3-propanediol (Aldrich) gave a 58.5% yield of 2-methyl-2-[[(phenanthro[3,2-b]thiophen-7-yl)methyl]amino]-1,3-propanediol methanesulfonate, mp 220°–221°, (EtOH/Et$_2$O), (C,H,N,S).

EXAMPLE 48

2-Methyl-2-[[(3-methyl-3H-naphth[1,2-g]indol-1-yl)methyl]amino]-1,3-propanediol

48A. Ethyl 3-methyl-3H-naphth[1,2-g]indole-2-carboxylate

Using the procedure outlined in Example 34A except that dimethyl sulfate was used as the alkylating agent, ethyl 3H-naphth[1,2-g]indole-2-carboxylate (H. G. Pars Pharmaceutical Laboratories, Inc.) gave a 74.5% yield of ethyl 3-methyl-3H-naphth[1,2-g]indol-2-carboxylate, mp 136°–138°, (CH$_2$Cl$_2$/hexane), (C,H,N).

48B. 3-Methyl-3H-naphth[1,2-g]indole-1-carbaldehyde·0.27 H$_2$O

Ethyl 3-methyl-3H-naphth[1,2-g]indole-2-carboxylate (48A) was formylated using the procedure of A. Rieche et al., Chem. Ber. 93, 88 (1960). The reaction mixture was partially purified by chromatography (SiO$_2$/CH$_2$Cl$_2$) and the fractions containing the aldehyde-ester combined and hydrolyzed as described in Example 15B to give a crude aldehyde-acid which was decarboxylated directly as described in Example 15B to give a crude aldehyde. After chromatography (SiO$_2$/PhCH$_3$), a 51.7% overall yield of 3-methyl-3H-naphth[1,2-g]indole-1-carbaldehyde·0.27 H$_2$O, mp 196°–197°, (CH$_2$Cl$_2$), (C,H,N) was obtained. In this case formylation gave only one aldehyde isomer. In other Examples where more than one isomer was produced, the mixtures of aldehyde-esters and aldehyde-acids were used with only partial purification to remove non-aldehydic material. The actual mixtures of crude target aldehydes were then separated by column chromatography on SiO$_2$ using either PhCH$_3$ or CH$_2$Cl$_2$ as the eluting solvent and further purified by crystallization if necessary.

48C. 2-Methyl-2-[[(3-methyl-3H-naphth[1,2-g]indol-1-yl)methyl]amino]-1,3-propanediol hydrochloride·0.33 H$_2$O Using the procedure outlined in Example 1, 3-methyl-3H-naphth[1,2-g]indole-1-carbaldehyde (48B) and 2-amino-2-methyl-1,3-propanediol (Aldrich) gave a 20.0% yield of 2-methyl-2-[[(3-methyl-3H-naphth[1,2-g]indol-1-yl)methyl]amino]-1,3-propanediol hydrochloride·0.33 H$_2$O, mp 234°–235° (dec), (CH$_3$OH/Et$_2$O), (C,H,N,Cl).

EXAMPLE 49

(±)-(2R*,3S*)-2-Methyl-2-[[(3-methyl-3H-naphth[1,2-g]indol-1-yl)methyl]amino]-1,3-butanediol methanesulfonate·0.60 H$_2$O To a RB flask was added (±)-(2R*,3S*)-2-amino-2-methyl-1,3-butanediol acetate (32F), an equimolar amount of sodium methoxide (MCB) and CH$_3$OH (100 mL). After warming, the solvent was removed by rotary evaporation, and after addition of 3-methyl-3H-naphth[1,2-g]indole-1-carbaldehyde (48B), the reaction run following the normal reductive amination procedure outlined in Example 1 to give a 49.9% yield of (±)-(2R*,3S*)-2-methyl-2-[[(3-methyl-3H-naphth[1,2-g]indol-1-yl)methyl]amino]-1,3-butanediol hydrochloride·0.60 H$_2$O, mp 220°–230° (gradual dec), (EtOH/Et$_2$O), (C,H,N,Cl).

EXAMPLE 50

2-Methyl-2-[[(3-methyl-3H-naphth[2,3-e]indol-11-yl)methyl]amino]-1,3-propanediol

50A. Ethyl 3-methyl-3H-naphth[2,3-e]indole-2-carboxylate

Using the procedure described in Example 34A except that dimethyl sulfate was used as the alkylating agent, ethyl 3H-naphth[2,3-e]indole-2-carboxylate (H. G. Pars Pharmaceutical Laboratories, Inc.) gave a 97% yield of ethyl 3-methyl-3H-naphth[2,3-e]indole-2-carboxylate, mp 141°–144°, (EtOAc/hexane), (C,H,N).

50B. 3-Methyl-3H-naphth[2,3-e]indole-11-carbaldehyde

Using the procedure described in Example 48B, ethyl 3-methyl-3H-naphth[2,3-e]indole-2-carboxylate (50A) gave a 35.9% yield of 3-methyl-3H-naphth[2,3-e]indole-11-carbaldehyde, mp 175°–176°, (PhCH$_3$), (C,H,N).

50C. 2-Methyl-2-[[(3-methyl-3H-naphth[2,3-e]indol-11-yl)methyl]amino]-1,3-propanediol hydrochloride·0.5 H$_2$O Using the procedure described in Example 1, 3-methyl-3H-naphth[2,3-e]indole-11-carbaldehyde (50B) and 2-amino-2-methyl-1,3-propanediol (Aldrich) gave a 69.0% yield of 2-methyl-2-[[(3-methyl-3H-naphth[2,3-e]indol-11-yl)methyl]amino]-1,3-propanediol hydrochloride·0.5 H$_2$O, mp>300° (darkens~200°), (CH$_3$OH/Et$_2$O), (C,H,N,Cl).

EXAMPLE 51

2-Methyl-2-[[(1-methyl-1H-naphth[2,3-g]indol-3-yl)methyl]amino]-1,3-propanediol

51A. Ethyl 1-methyl-1H-naphth[2,3-g]indole-2-carboxylate

Using the procedure outlined in Example 34A except that dimethyl sulfate was used as the alkylating agent, ethyl 1H-naphth[2,3-g]indole-2-carboxylate (H. G. Pars Pharmaceutical Laboratories, Inc.) gave a 96.2% yield of ethyl 1-methyl-1H-naphth[2,3-g]indole-2-carboxylate, mp 165°–165.5°, (CH$_2$Cl$_2$/hexane), (C,H,N).

51B. 1-Methyl-1H-naphth[2,3-g]indole-3-carbaldehyde 51C. 1-Methyl-1H-naphth[2,3-g]indole-5-carbaldehyde

51D.
1-Methyl-1H-naphth[2,3-g]indole-6-carbaldehyde·0.1 H₂O

Using the procedure described in Example 48B, ethyl 1-methyl-1H-naphth[2,3-g]indole-2-carboxylate (51A) gave a mixture of aldehydes which was purified by SiO₂ chromatography using CH₂Cl₂ for the first column then PhCH₃/CH₂Cl₂ mixtures for subsequent columns. Three aldehydes were obtained pure in this way: 1-methyl-1H-naphth[2,3-g]indole-3-carbaldehyde, mp 182°–183°, (PhCH₃), (C,H,N), R$_f$=0.11 (SiO₂/CH₂Cl₂), 22.2% yield; 1-methyl-1H-naphth[2,3-g]indole-5-carbaldehyde, mp 128°–131°, (PhCH₃), (C,H,N), R$_f$=0.32 (SiO₂/CH₂Cl₂), 32.3% yield; 1-methyl-1H-naphth[2,3-g]indole-6-carbaldehyde·0.1 H₂O, mp 156.5°–159°, isolated directly from column, (C,H,N), R$_f$=0.5 (SiO₂/CH₂Cl₂), 4.4% yield.

51E.
2-Methyl-2-[[(1-methyl-1H-naphth[2,3-g]indol-3-yl)methyl]amino]-1,3-propanediol hydrochloride Using the procedure outlined in Example 1, 1-methyl-1H-naphth[2,3-g]indole-3-carbaldehyde (51B) and 2-amino-2-methyl-1,3-propanediol (Aldrich) gave a 54.0% yield of 2-methyl-2-[[(1-methyl-1H-naphth[2,3-g]indol-3-yl)methyl]amino]-1,3-propanediol hydrochloride, mp 278°–280°, (CH₃OH/Et₂O), (C,H,N,Cl).

EXAMPLE 52
2-Methyl-2-[[(1-methyl-1H-naphth[2,3-g]indol-5-yl)methyl]amino]-1,3-propanediol hydrochloride·0.25 H₂O Using the procedure outlined in Example 1, 1-methyl-1H-naphth[2,3-g]indole-5-carbaldehyde (51C) and 2-amino-2-methyl-1,3-propanediol (Aldrich) gave a 61.1% yield of 2-methyl-2-[[(1-methyl-1H-naphth[2,3-g]indol-5-yl)methyl]amino]-1,3-propanediol hydrochloride·0.25 H₂O, mp ~300° (dec, darkens at 264°), (EtOH/Et₂O), (C,H,N,Cl).

EXAMPLE 53
2-Methyl-2-[[(1-methyl-1H-[1]benzothieno[2,3-g]indol-3-yl)methyl]amino]-1,3-propanediol

53A. Ethyl 1-methyl-1H-[1]benzothieno[2,3-g]indole-2-carboxylate

Using the procedure outlined in Example 34A except that dimethyl sulfate was used as the alkylating agent, ethyl 1H-[1]benzothieno[2,3-g]indole-2-carboxylate (H. G. Pars Pharmaceutical Laboratories, Inc.) gave a quantitative yield of ethyl 1-methyl-1H-[1]benzothieno[2,3-g]indole-2-carboxylate, mp 85°–86°, (PhCH₃), (C,H,N).

53B. Ethyl 3-formyl-1-methyl-1H-[1]benzothieno[2,3-g]indole-2-carboxylate

Ethyl 1-methyl-1H-[1]benzothieno[2,3-g]indole-2-carboxylate (53A) was formylated by the procedure of A. Rieche et al., Chem. Ber. 93, 88 (1960) to give a 58.7% yield of ethyl 3-formyl-1-methyl-1H-[1]benzothieno[2,3-g]indole-2-carboxylate, mp 145°–147°, (CH₂Cl₂/hexane), (C,H,N).

53C.
1-Methyl-1H-[1]benzothieno[2,3-g]indole-3-carbaldehyde

Using the procedure outlined in 15B, ethyl 3-formyl-1-methyl-1H-[1]benzothieno[2,3-g]indole-2-carboxylate gave a 31.8% yield of 2-methyl-1H-[1]benzothieno[2,3-g]indole-3-carbaldehyde, mp 192°–194°, (CH₂Cl₂/petroleum ether), (C,H,N).

53D.
2-Methyl-2-[[(1-methyl-1H-[1]benzothieno[2,3-g]indol-3-yl)methyl]amino]-1,3-propanediol hydrochloride Using the procedure outlined in Example 1, 1-methyl-1H-[1]benzothieno[2,3-g]indole-3-carbaldehyde (53C) and 2-amino-2-methyl-1,3-propanediol (Aldrich) gave a 56.7% yield of 2-methyl-2-[[(1-methyl-1H-[1]benzothieno[2,3-g]indol-3-yl)methyl]amino]-1,3-propanediol hydrochloride, mp 228°–230° (dec), (CH₃OH/Et₂O), (C,H,N,Cl).

EXAMPLE 54
2-[[(6-Ethyl-1,6-dihydro-1-methylpyrrolo[3,2-c]carbazol-3-yl)methyl]amino]-2-methyl-1,3-propanediol

54A. Ethyl 6-ethyl-1,6-dihydro-1-methylpyrrolo[3,2-c]carbazole-2-carboxylate Using the procedure outlined in Example 34A, ethyl 6-ethyl-1,6-dihydropyrrolo[3,2-c]carbazole-2-carboxylate (H. G. Pars Pharmaceutical Laboratories, Inc.) gave a 90.5% yield of ethyl 6-ethyl-1,6-dihydro-1-methylpyrrolo[3,2-c]carbazole-2-carboxylate, mp 115.5°–116°, (CH₂Cl₂/hexane), (C,H,N).

54B.
6-Ethyl-1,6-dihydro-1-methylpyrrolo[3,2-c]carbazole-3-carbaldehyde

Using the procedure outlined in Example 48B, ethyl 6-ethyl-1,6-dihydro-1-methylpyrrolo[3,2-c]carbazole-2-carboxylate gave a 9.3% yield of 6-ethyl-1,6-dihydro-1-methylpyrrolo[3,2-c]carbazole-3-carbaldehyde, mp 144°–146°, (CH₂Cl₂), (C,H,N).

54C.
2-[[(6-Ethyl-1,6-dihydro-1-methylpyrrolo[3,2-c]carbazol-3-yl)methyl]amino]-2-methyl-1,3-propanediol hydrochloride·0.6 H₂O Using the procedure described in Example 1, 6-ethyl-1,6-dihydro-1-methylpyrrolo[3,2-c]carbazole-3-carbaldehyde (54B) and 2-amino2-methyl-1,3-propanediol (Aldrich) gave a 48.3% yield of 2-[[(6-ethyl-1,6-dihydro-1-methylpyrrolo[3,2-c]carbazol-3-yl)methyl]amino]-2-methyl-1,3-propanediol hydrochloride·0.6 H₂O, mp 265°–267°, (EtOH/Et₂O), (C,H,N,Cl).

EXAMPLE 55
2-Methyl-2-[[(1-methyl-1H-benzofuro[2,3-g]indol-3-yl)methyl]amino]-1,3-propanediol

55A. Ethyl 1-methyl-1H-benzofuro[2,3-g]indole-2-carboxylate

Using the procedure outlined in Example 34A, ethyl 1H-benzofuro[2,3-g]indole-2-carboxylate (H. G. Pars Pharmaceutical Laboratories, Inc.) gave a 86.3% yield of ethyl 1-methyl-1H-benzofuro[2,3-g]indole-2-carboxylate, mp 114°–116°, (EtOAc), (C,H,N).

55B. Ethyl 3-formyl-1-methyl-1H-benzofuro[2,3-g]indole-2-carboxylate

Ethyl 1-methyl-1H-benzofuro[2,3-g]indole-2-carboxylate (55A) was formylated according to the procedure of A. Rieche et al., Chem. Ber. 93, 88 (1960) to give an 82.5% yield of ethyl 3-formyl-1-methyl-1H-benzofuro[2,3-g]indole-2-carboxylate, mp 190°–192°, (CH$_2$Cl$_2$/hexane), (C,H,N).

55C. 1-Methyl-1H-benzofuro[2,3-g]indole-3-carbaldehyde

Using the procedure outlined in Example 15B, ethyl 3-formyl-1-methyl-1H-benzofuro[2,3-g]indole-3-carbaldehyde gave a 28.1% yield of 1-methyl-1H-benzofuro[2,3-g]indole-3-carbaldehyde, mp 163°–165°, (CH$_2$Cl$_2$/petroleum ether), (C,H,N).

55D. 2-Methyl-2-[[(1-methyl-1H-benzofuro[2,3-g]indol-3-yl)methyl]amino]-1,3-propanediol hydrochloride Using the procedure outlined in Example 1, 1-methyl-1H-benzofuro[2,3-g]indole-3-carbaldehyde (55C) and 2-amino-2-methyl-1,3-propanediol (Aldrich) gave a 63.9% yield of 2-methyl-2-[[(1-methyl-1H-benzofuro[2,3-g]indol-3-yl)methyl]amino]-1,3-propanediol hydrochloride, mp 234°–236°, (EtOH/Et$_2$O), (C,H,N,Cl).

EXAMPLE 56

2-Methyl-2-[[(3-methyl-3H-[1]benzothieno[2,3-e]indol-1-yl)methyl]amino]-1,3-propanediol hydrochloride

56A. 3-Methyl-3H-[1]benzothieno[2,3-e]indole-1-carbaldehyde·0.25 H$_2$O

Using the procedure outlined in Example 34A except that dimethyl sulfate was used as the alkylating agent, ethyl 3H-[1]benzothieno[2,3-e]indole-2-carboxylate (H. G. Pars Pharmaceutical Laboratories, Inc.) gave a nearly quantitative yield of crude ethyl 3-methyl-3H-[1]benzothieno[2,3-e]indole-2-carboxylate. This material was formylated using the procedure of A. Rieche et al., Chem. Ber. 93, 88 (1960) to give a crude mixture of aldehydes which was hydrolyzed and decarboxylated without purification using the procedure outlined in Example 15B to give a 19.0% yield of 3-methyl-3H-[1]benzothieno[2,3-e]indole-1-carbaldehyde·0.25 H$_2$O, mp 223.5°–224°, (CH$_2$Cl$_2$/hexane), (C,H,N).

56B. 2-Methyl-2-[[(3-methyl-3H-[1]benzothieno[2,3-e]indol-1-yl)methyl]amino]-1,3-propanediol hydrochloride Using the procedure described in Example 1, 3-methyl-3H-[1]benzothieno[2,3-e]indole-1-carbaldehyde (56A) and 2-amino-2-methyl-1,3-propanediol (Aldrich) gave a 41.4% yield of 2-methyl-2-[[(3-methyl-3H-[1]benzothieno[2,3-e]indol-1-yl)methyl]amino]-1,3-propanediol hydrochloride, mp 228°–230°, (CH$_3$OH/Et$_2$O), (C,H,N,Cl).

EXAMPLE 57

2-Hydroxymethyl-2-[[(7-methyl-7H-benzo[c]carbazol-10-yl)methyl]amino]-1,3-propanediol hydrochloride Using the procedure outlined in Example 1, 7-methyl-7H-benzo[c]carbazole-10-carbaldehyde (4B) and tris(hydroxymethyl)aminomethane (Aldrich) gave a 57.7% yield of 2-hydroxymethyl-2-[[(7-methyl-7H-benzo[c]carbazol-10-yl)methyl]amino]-1,3-propanediol hydrochloride, mp 203°–204.5°, (CH$_3$OH/Et$_2$O), (C,H,N,Cl).

EXAMPLE 58

2-Hydroxymethyl-2-[[(7-methyl-7H-benzo[c]carbazol-5-yl)methyl]amino]-1,3-propanediol hydrochloride Using the procedure outlined in Example 1, 7-methyl-7H-benzo[c]carbazole10-carbaldehyde (4B) and tris(hydroxymethyl)aminomethane (Aldrich) gave a 57.7% yield of 2-hydroxymethyl-2-[[(7-methyl-7H-benzo[c]carbazol-5-yl)methyl]amino]-1,3-propanediol hydrochloride, mp 245°–248° (dec), (CH$_3$OH/Et$_2$O), (C,H,N,Cl).

EXAMPLE 59

2-[[(Benzo[b]naphtho[2,3-d]thiophen-4-yl)methyl]amino]-2-methyl-1,3-propanediol

59A. Benzo[b]naphtho[2,3-d]thiophene-4-carbaldehyde

To a 3-necked RB flask equipped with magnetic stirring bar, septum, addition funnel and N$_2$ inlet line was added benzo[b]naphtho[2,3-d]thiophene (Cambridge Chemicals, Inc., 8.96 g, 38.24 mmol), TMEDA (Aldrich, 10.22 g, 87.93 mmol, 13.27 mL) and THF (250 mL). The mixture was cooled to −78°. A 2.3M solution of sec-BuLi (Aldrich, 67.64 mL, 87.93 mmol) was added dropwise to the mixture over 30 min. The now deep-red solution was allowed to warm to 0° for 10 min and cooled back down to −78°. To the solution was added DMF (Aldrich, 9.78 g, 0.134 mol, 10.36 mL) by syringe in one portion over 2 min. The dry-ice bath was removed and the mixture allowed to warm to RT. After 3 h the reaction was diluted with H$_2$O (1 L) and acidified to pH=6 with 1N HCl. The mixture was extracted with EtOAc (3×1 L). The EtOAc layers were combined and washed sequentially with H$_2$O (3×500 mL), saturated NaCl solution (3×500 mL), dried (Na$_2$SO$_4$), filtered and the solvent removed to give, after drying, 11.81 g of crude product. NMR analysis showed this mixture to contain starting material and two aldehydes, benzo[b]naphtho[2,3-d]thiophene-4-carbaldehyde and benzo[b]naphtho[2,3-d]thiophene-6-carbaldehyde (7A) in a 7:3 ratio, respectively.

The aldehydes were not separable by TLC and fractional crystallization failed to give any resolution of the mixture. The crude mixture was dissolved in THF (300 mL) and treated with solid NaBH$_4$ (Aldrich, 0.85 g, 22.4 mmol). After stirring overnight H$_2$O (10 mL) was added to the mixture and the solvent removed. The crude product was dissolved with difficulty in EtOAc (3 L) and washed with H$_2$O (1 L), saturated NaCl (1 L), dried (Na$_2$SO$_4$), filtered and the solvent removed to give 9.93 g of white solid. TLC analysis (SiO$_2$/CH$_2$Cl$_2$) of the material showed two low R$_f$ spots corresponding to 4-hydroxymethyl-benzo[b]naphtho[2,3-d]thiophene (R$_f$=0.27) and 6-hydroxymethyl-benzo[b]naphtho[2,3-d]thiophene (R$_f$=0.32). Fractional crystallization using EtOAc gave 2.97 g of pure 4-hydroxymethyl-benzo[b]naphtho[2,3-d]thiophene (29.2% yield) which was then oxidized with barium manganate as outlined in Example 14B to give 2.80 g (94.9% yield) of benzo[b]naphtho[2,3-d]thiophene-4-carbaldehyde, mp 201.5°–203.5°, isolated directly from chromatography, (C,H,S).

59B.
2-[[(Benzo[b]naphtho[2,3-d]thiophen-4-yl)methyl]amino]-2-methyl-1,3-propanediol methanesulfonate Using the procedure outlined in Example 1, benzo[b]naphtho[2,3-d]thiophene-4-carbaldehyde (59A) and 2-amino-2-methyl-1,3-propanediol (Aldrich) gave a 48.8% yield of 2-[[(benzo[b]naphtho[2,3-d]thiophen-4-yl)methyl]amino]-2-methyl-1,3-propanediol methanesulfonate, mp 208.5°–210°, (EtOH/Et$_2$O), (C,H,N,S).

EXAMPLE 60
2-[[(Benzo[b]naphtho[1,2-d]thiophen-10-yl)methyl]amino]-2-methyl-1,3-propanediol

60A.
10-(Bromomethyl)-benzo[b]naphtho[1,2-d]thiophene

Using the procedure outlined in 6A, 10-methyl-benzo[b]naphtho[1,2-d]thiophene (H. G. Pars Pharmaceutical Laboratories, Inc.) gave a 39.0% yield of 10-(bromomethyl)-benzo[b]naphtho[1,2-d]thiophene, mp 202°–203°, (CH$_2$Cl$_2$), (C,H,Br,S).

60B.
2-[[(Benzo[b]naphtho[1,2-d]thiophen-10-yl)methyl]amino]-2-methyl-1,3-propanediol methanesulfonate Using the procedure outlined in Example 6B, 10-(bromomethyl)-benzo[b]naphtho[1,2-d]thiophene (60A) and 2-amino-2-methyl-1,3-propanediol (Aldrich) gave a 39.7% yield of 2-[[(benzo[b]naphtho[1,2-d]thiophen-10-yl)methyl]amino]-2-methyl-1,3-propanediol methanesulfonate, mp 213°–214°, (EtOH/Et$_2$O), (C,H,N,S).

EXAMPLE 61
(±)-3-Methoxy-2-methyl-2-[[(7-methyl-7H-benzo[c]carbazol-10-yl)methyl]amino]-1,3-propanediol

61A.
4-Aza-3-hydroxymethyl-3-methyl-1-oxaspiro[4.5]decane

A solution of 2-amino-2-methyl-1,3-propanediol (Aldrich, 303.4 g, 3.0 mol), cyclohexanone (Fisher, 294.5 g, 3.0 mol) and PhCH$_3$ (400 mL) was refluxed for approximately 2 h with azeotropic removal of H$_2$O. The material which crystallized from the PhCH$_3$ on cooling was recrystallized 2× from hexane to give 444.4 g of 4-aza-3-hydroxymethyl-3-methyl-1-oxaspiro[4.5]decane (80%) mp 52°–54°, (C,H,N).

61B.
4-Aza-3-methoxymethyl-3-methyl-1-oxaspiro[4.5]decane

A mechanically stirred 60% dispersion of NaH in mineral oil (Morton Thiokol, Inc. - Alfa Products, 75 g, 1.9 mol) was washed with dry hexane to remove the oil and suspended in dry DMF (200 mL). To the mixture was added a solution of 4-aza-3-hydroxymethyl-3-methyl-1-oxaspiro[4.5]decane (61A, 27.8 g, 1.5 mol) in dry DMF (200 mL) keeping the reaction mixture temperature between 30°–35°. Small amounts of DMF were added as necessary to facilitate stirring. The mixture was stirred at RT for 1.5 h, then cooled and treated with methyl iodide (Fisher, 234.2 g, 102.7 mL, 1.65 mol) keeping the reaction temperature between 20°–30°. The mixture was stirred 2 h at RT and slowly treated with abs. EtOH (40 mL), then diluted with dry Et$_2$O (3 L). The reaction mixture was filtered, and the solvent removed by rotary evaporation. The residue was then fractionally distilled to give 209.7 g (70.3%) of 4-aza-3-methoxymethyl-3-methyl-1-oxaspiro[4.5]decane as a colorless liquid, bp 144°/14 mm, (C,H,N).

61C. 2-Amino-3-methoxy-2-methyl-1-propanol

A solution of 4-aza-3-methoxymethyl-3-methyl-1-oxaspiro[4.5]decane (61B, 299 g, 1.5 mol) and 6N HCl (500 mL) was refluxed for 60 min. On cooling, two layers formed, the upper one containing cyclohexanone was removed by extraction with Et$_2$O (2×400 mL). The lower aqueous layer was concentrated on a rotary evaporator to give a syrup which then was treated with excess 50% NaOH. The resulting slurry was extracted with Et$_2$O/CH$_2$Cl$_2$ (2:1, 4×500 mL), then with CH$_2$Cl$_2$ (500 mL). The solvent was removed by rotary evaporation to give 198 g of pale oil. Fractional distillation of this oil gave 166 g (93%) of 2-amino-3-methoxymethyl-1-propanol as a colorless oil, bp 94°/17 mm, (C,H,N).

61D.
(±)-3-Methoxy-2-methyl-2-[[(7-methyl-7H-benzo[c]carbazol-10-yl)methylamino]-1,3-propanediol hydrochloride.0.2 H$_2$O Using the procedure outlined in Example 1, 7-methyl-7H-benzo[c]carbazole-10-carbaldehyde (4B) and (±)-2-amino-3-methoxy-2-methyl-1-propanol (61 C) gave a 39.6% yield of (±)-3-methoxy-2-methyl-2-[[(7-methyl-7H-benzo[c]carbazol-10-yl)methyl]amino]-1,3-propanediol hydrochloride·0.2 H$_2$O, mp 194°–196°, (i-PrOH/Et$_2$O), (C,H,N,Cl).

EXAMPLE 62
[1,1-Bis-(methoxymethyl)ethyl]-[(7-methyl-7H-benzo[c]carbazol-10-yl)methyl]amine

62A. 1,1-Bis-(methoxymethyl)ethylamine

To a 3-necked 3 L RB flask equipped with overhead stirrer, condenser and N$_2$ inlet line was added NaH (Morton Thiokol, Inc. - Alfa Products, 60% in mineral oil, 44 g, 1.1 mol). After washing with hexane (3×200 mL), dry THF (1.1 L) was added to the flask. After cooling to 0°, 2-amino-3-methoxy-2-methyl-1-propanol (61C, 119.16 g, 1.0 mol) was added dropwise to the flask at such a rate that the reaction temperature remained below 30°. The resulting slurry was cooled to 0°. Iodomethane (Aldrich, 141.94 g, 1.0 mol, 62.25 mL) was added dropwise to the mixture at such a rate that the reaction temperature remained below 30°. After the mixture was stirred for 1 h, EtOH (25 mL) was added to quench the reaction. The volume of the reaction was reduced to 200 mL. This material was diluted to 2 L with Et$_2$O, filtered and the solvent removed. Fractional distillation of this material gave 91.02 g (68.3% yield of 1,1-bis-(methoxymethyl)ethylamine, bp 146°–149°, (C,H,N).

62B.
[1,1-Bis-(methoxymethyl)ethyl]-[(7-methyl-7H-benzo[c]carbazol-10-yl)methyl]amine hydrochloride Using the procedure outlined in Example 1, 7-methyl-7H-benzo[c]carbazole-10-carbaldehyde (4B) and 1,1-bis-(methoxymethyl)ethylamine (62A) gave a 28.1% yield of [1,1-bis-(methoxymethyl)ethyl]-[(7-methyl-7H-benzo[c]carbazol-10-yl)methyl]amine hydrochloride, mp 209.5°–210°, (EtOH/hexane), (C,H,N,Cl).

EXAMPLE 63

2-Isopropyl-2-[[(7-methyl-7H-benzo[c]carbazol-10-yl)methyl]amino]-1,3-propanediol

63A. 2-Isopropyl-2-nitro-1,3-propanediol

To a solution of 2-methyl-1-nitropropane (38.7 g, 0.375 mol, prepared by the procedure of N. Kornblum, B. Tunbe, and H. Ungnade, *J. Amer. Chem. Soc.*, 76, 3209 (1954)) and NEt$_3$ (Eastman, 3.79 g, 0.0375 mol) in CH$_3$OH (50 mL) was added dropwise 37% aqueous formaldehyde solution (Mallinckrodt, 76.2 g, 0.938 mol) at a rate such that the reaction mixture temperature did not exceed 30°. After 72 h, the solution was concentrated under vacuum and the residue was dissolved in H$_2$O (250 mL). The solution was continuously extracted for 1 h with CH$_2$Cl$_2$ (1 L). The CH$_2$Cl$_2$ solution was dried (MgSO$_4$), filtered, and concentrated to give 53.3 g (87%) of 2-isopropyl-2-nitro-1,3-propanediol, as a waxy, white solid, mp 67°–72° C. (lit. mp 87°–88°, B. M. Vanderbilt and H. B. Hass, *Ind. Eng. Chem.* 32, 34 (1940). In our hands this literature procedure failed to give the desired compound).

63B. 2-Amino-2-isopropyl-1,3-propanediol acetate

Using the procedure in 32E, 2-isopropyl-2-nitro-1,3-propanediol (63A) gave a 98% yield of 2-amino-2-isopropyl-1,3-propanediol acetate, mp 155°–155.5°, (C,H,N). H. S. Broadbent et al., *J. Heterocyclic Chem.* 13, 337 (1975) report the synthesis of this compound as the free base (mp 70°–72°).

63C. 2-Isopropyl-2-[[(7-methyl-7H-benzo[c]carbazol-10-yl)methyl]amino]-1,3-propanediol hydrochloride To a RB flask was added 2-amino-2-isopropyl-1,3-propanediol acetate (63B), an equimolar amount of sodium methoxide (MCB) and CH$_3$OH (100 mL). After warming, the solvent was removed by rotary evaporation, and after addition of 7-methyl-7H-benzo[c]carbazole-10-carbaldehyde (4B), the reaction run following the normal reductive amination procedure outlined in Example 1 to give a 48.6% yield of 2-isopropyl-2-[[(7-methyl-7H-benzo[c]carbazol-10-yl)methyl]amino]-1,3-propanediol hydrochloride, mp 219°–220.5°, (CH$_3$OH/Et$_2$O), (C,H,N,Cl).

EXAMPLE 64

2β-[[(7-Methyl-7H-benzo[c]carbazol-10-yl)methyl]amino]-1α,3α-cyclohexanediol hydrochloride

64A. 1α,2β,3α-2-Amino-1,3-cyclohexanediol acetate

This compound was prepared by the method of F. Lichtenthaler (*Ber.* 96, 846 (1963), mp 175°–177°, (C,H,N), (lit. 178°–179°, F. Lichtenthaler (*Ber.* 96, 846 (1963)).

64B. 2β-[[(7-Methyl-7H-benzo[c]carbazol-10-yl)methyl]amino]-1α,3α-cyclohexanediol hydrochloride·H$_2$O To a RB flask was added 1α,2β,3α-2-amino-1,3-cyclohexanediol acetate (64A), an equimolar amount of sodium methoxide (MCB) and CH$_3$OH (100 mL). After warming, the solvent was removed by rotary evaporation, and after addition of 7-methyl-7Hbenzo[c]carbazole-10-carbaldehyde (4B), the reaction run following the normal reductive amination procedure outlined in Example 1 to give a 27.8% yield of 2β-[[(7-methyl-7H-benzo[c]carbazol-10-yl)methyl]amino]-1α,3α-cyclohexanediol hydrochloride, mp 233°–234°, (EtOH/hexane), (C,H,N,Cl).

EXAMPLE 65

2-[[(7-Methyl-7H-benzo[c]carbazol-10-yl)methyl]amino]-2-pentyl-1,3-propanediol

65A. 2-Pentyl-2-nitro-1,3-propanediol

To a rapidly stirred mixture of 1-nitrohexane (Aldrich, 23 g, 0.175 mol) and calcium hydroxide (Fisher, 54 mg) at RT was added dropwise during 10 min a 37% aqueous formaldehyde solution (Mallinckrodt, 28.8 g). A two-phase liquid mixture resulted, and no temperature change was observed during the addition of the formaldehyde solution. During the first 0.5 h, the temperature gradually rose to 30°. A water bath was then used to keep the reaction temperature below 30°. After 1 h, the bath was removed and stirring was continued for 20 h. The mixture was treated with excess solid CO$_2$ (~100 mg). Precipitated CaCO$_3$ was removed by filtration. The residue was washed with H$_2$O (5 mL) and then with CH$_2$Cl$_2$ (3×5 mL). The filtrate (including washes) was shaken with CH$_2$Cl$_2$ (500 mL). The layers were then separated. The aqueous layer was extracted with additional CH$_2$Cl$_2$ (3×10 mL). The combined organic layers were washed with saturated NaCl (15 mL), dried (MgSO$_4$), filtered, concentrated, and dried under vacuum at RT, to give 31.5 g (94.2%) of 2-pentyl-2-nitro-1,3-propanediol as a waxy white solid mp 54–55 (lit. 53°–55°, T. Urbanski and B. Chylinska, *Roczniki Chemii* 31, 695 (1957)). These workers reported that this compound could not be prepared by the method of B. M. Vanderbilt and H. B. Hass, *Industrial and Engineering Chemistry* 32, 34 (1940). The above procedure is in fact an adaptation of the method of Vanderbilt and Hass.) (C,H,N).

65B. 2-Amino-2-(hydroxymethyl)heptanol acetate

Using the procedure outlined in Example 32E, 2-pentyl-2-nitro-1,3-propanediol (65A) gave 2-amino-2-(hydroxymethyl)heptanol acetate in 75.6% yield, mp>72° dec, (C,H,N).

65C. 2-[[(7-Methyl-7H-benzo[c]carbazol-10-yl)methyl]amino]-2-pentyl-1,3-propanediol hydrochloride To a RB flask was added 2-amino-2-(hydroxymethyl)heptanol acetate (65B), an equimolar amount of sodium methoxide (MCB) and CH$_3$OH (100 mL). After warming, the solvent was removed by rotary evaporation, and after addition of 7-methyl-7H-benzo[c]carbazole-10-carbaldehyde (4B), the reaction run following the normal reductive amination procedure outlined in Example 1 to give a 39.3% yield of 2-[[(7-methyl-7H-benzo[c]carbazol-10-yl)methyl]amino]-2-pentyl-1,3-propanediol hydrochloride, mp 191.5°–192.5°, (EtOH/Et$_2$O), (C,H,N,Cl).

EXAMPLE 66

3-Methoxy-2-(methoxymethyl)-2-[[(7-methyl-7H-benzo[c]carbazol-10-yl)methyl]amino]propanol

66A. 4-Aza-3,3-bis-(methoxymethyl)-1-oxaspiro[4.5]decane

To a 3-necked RB flask equipped with mechanical stirrer, thermometer condenser and N$_2$ inlet line was added a 60% dispersion of NaH in mineral oil (Morton Thiokol, Inc. - Alfa Products, 21.1 g, 0.55 mol) (washed with hexane (3×200 mL) to remove the oil) and 500 mL of dry DMF. A slurry of 4-aza-3,3-bis-(hydroxymethyl)-1-oxaspiro [4.5]decane (prepared using the procedure of J. S. Pierce et al., *J. Amer. Chem. Soc.* 73, 2595 (1951), 100.63 g, 0.50 mol) in dry DMF (125 mL) was added slowly to the flask. The mixture was stirred at RT for 1 h and then cooled to 5°. Iodomethane (Aldrich, 78.07 g, 0.55 mol, 34.3 mL) was then slowly added dropwise to the mixture. Extensive frothing occurred. After addition of iodomethane was completed the reaction was stirred for 30 min. This mixture was quickly transferred to a large-bore addition funnel and added to the same amount of a 60% NaH dispersion (21.1 g, 0.55 mol) and dry DMF (200 mL) in a 3-neck RB flask equipped with mechanical stirrer, thermometer, condenser and $N_2$ inlet line as above. After stirring for 1 h, the mixture was cooled and iodomethane (Aldrich, 78.07 g, 0.55 mol, 34.3 mL) added as above. The mixture was stirred overnight and diluted with $Et_2O$ to a volume of 6 L and filtered to remove inorganic salts. The solvent was then removed by rotary evaporation to give a crude oil. This material (97.2 g, 84.8%) was then distilled and the fraction boiling between 134°–143°/15 mm collected. This material was mainly 4-aza-3,3-bis-(methoxymethyl)-1-oxaspiro[4.5]decane accompanied by 4% of the corresponding —$NCH_3$ compound as shown by GLC (10% OV-17 on Chromasorb W at 170°). This material was used in the next step without further purification. 66B. 2-Amino-2,2-bis-(methoxymethyl)ethanol acetate A mixture of crude 4-aza-3,3-bis-(methoxymethyl)-1-oxaspiro[4.5]decane (66A, 40.0 g, 0.174 mol) and 6N HCl (100 mL) was refluxed for 1 h. The mixture was cooled and washed with $Et_2O$ (3×100 mL). The volume of the aqueous layer was reduced to 25 mL by rotary evaporation, basified with excess 50% NaOH solution and extracted with a mixture of $Et_2O/CH_2Cl_2$ (3:1, 2×200 mL). The organic layers were combined, the solvent removed and the resulting crude oil distilled to give 16.4 g (63.2%) of 2-amino-2,2-bis-(methoxymethyl)ethanol, (bp 109°–110°/15 mm). This material also contains some of the —$NCH_3$ compound. This material was further purified by conversion to the —$NCH_2Ph$ derivative. Thus, a mixture of crude 2-amino-2,2-bis-(methoxymethyl)ethanol (15.0 g, ~0.10 mol), benzaldehyde (Aldrich, 7.42 g, 0.07 mol), $NaBH_3CN$ (Aldrich, 4.4 g, 0.07 mol) and $CH_3OH$ (100 mL) was stirred at 5° for 15 min then at RT for 2 h. $H_2O$ (50 mL) then excess 12N HCl was then added to the flask. The volume of the mixture was reduced to 50 mL by rotary evaporation. The mixture was washed with $Et_2O$ (100 mL), basified with 50% NaOH solution and extracted with $Et_2O$ (200 mL). After removal of the solvent the crude oil (15.54 g) was distilled to give 11.64 g of 2-benzylamino-2,2-bis-(methoxymethyl)ethanol, bp 118°–119°/0.10 mm, shown to 99.7% pure by GLC (10% OV-17 on Chromasorb W at 250°), (C,H,N). A mixture of 2-benzylamino-2,2-bis-(methoxymethyl)ethanol (8.25 g, 0.0345 mol), 5% Pd/C (Aldrich, 1.0 g), abs. EtOH (250 mL) and glacial HOAc (25 mL) was hydrogenated in a Parr apparatus at 40 psi for 15 min. The catalyst was removed by filtration through a pad of Celite ® and the solvent removed to give the crude product which after crystallization from abs. EtOH gave a 48.6% yield of 2-amino-2,2-bis-(methoxymethyl)ethanol acetate, mp 119.5°–120.5°, (C,H,N).

66C. 3-Methoxy-2-(methoxymethyl)-2-[[(7-methyl-7H-benzo[c]carbazol-10-yl)methyl]amino]propanol hydrochloride To a RB flask was added 2-amino-2,2-bis-(methoxymethyl)ethanol acetate (66B), an equimolar amount of sodium methoxide (MCB) and $CH_3OH$ (100 mL). After warming, the solvent was removed by rotary evaporation, and after addition of 7-methyl-7H-benzo[c]carbazole-10-carbaldehyde (4B), the reaction run following the normal reductive amination procedure outlined in Example 1 to give a 9.7% yield of 3-methoxy-2-(methoxymethyl)-2-[[(7-methyl-7H-benzo[c]carbazol-10-yl)methyl]amino]propanol hydrochloride, mp 159°–160°, (EtOH/$Et_2O$), (C,H,N,Cl).

EXAMPLE 67

2-Methyl-2-[[(7-methyl-7H-benzo[c]carbazol-10-yl)methyl]amino]-1,4-butanediol hydrochloride 67A. Ethyl N-benzylidene-1-alaninate Ethyl N-benzylidene-1-alaninate was prepared according to the general procedure of G. Stork et. al., *J. Org. Chem.* 41, 349 (1976), bp 98°–100°/0.4 mm (lit., 100°/0.3 mm, A. Calcagni et al., *Synthesis* 445 (1981)).

67B. 2-(2-Iodoethoxy)tetrahydro-2-H-pyran

Freshly distilled dihydropyran (Aldrich, 59.0-g, 0.7 mol) was added dropwise to a cooled solution of 2-iodoethanol (Aldrich, 98 g, 0.57 mol) in $Et_2O$ (1 L) containing 0.1 g of p-toluenesulfonic acid (Eastman). The solution was then stirred for 1 h at 5°. Solid $K_2CO_3$ (Mallinckrodt, 5 g) was then added to the reaction mixture and the resulting suspension stirred an additional 1 h at RT. The reaction was then filtered and the remaining solid washed with $Et_2O$ (1 L). The organic solutions were combined and concentrated rotary evaporation (in a flask washed with 1% $NEt_3$ in $H_2O$). The crude 2-(2-iodoethoxy)tetrahydro-2-Hpyran (~100 g, 68.9%) was used without further purification.

67C. Ethyl 2-benzylideneamino-2-methyl-4-[(tetrahydro-2H-pyran-2-yl)oxy]butyrate A solution of lithium diisopropylamide was prepared by dropwise addition of n-BuLi (Aldrich 1.6M in hexane, 228 mL, 0.365 mol) to a solution of diisopropylamine (Aldrich, 51.6 g, 0.51 mol) in a mixture of dry THF (700 mL) and dry HMPA (Aldrich, 40 mL) kept at 30°–40°. The solution was then cooled to −70° and a solution of ethyl N-benzylidene-1-alaninate (67A, 74.9 g, 0.365 mol) was added dropwise to the solution allowing the reaction mixture warm to −20° for several min. The resulting red solution was then cooled to −70°. 2-(2-Iodoethoxy)tetrahydro-2H-pyran (67B, 98.1 g, 0.383 mol) was then added to the solution at such a rate that the temperature in the reaction mixture did not rise above −65°. The solution was allowed to warm slowly to RT and stirred for 14 h. The volume of the solution was reduced to ~300 mL by a stream of dry $N_2$ during the last few hours to facilitate the final workup. The reaction was quenched with saturated NaCl (800 mL) and diluted with $Et_2O$ (800 mL). The $Et_2O$ was removed and the aqueous layer extracted with hexane (500 mL). The $Et_2O$ and hexane layers were combined and dried ($Na_2SO_4$). The solution was filtered and the solvent removed to give 124 g of crude red oil. Bulb to bulb distillation (in 1% aqueous NEt₃ washed glassware) 210° bath temperature/0.3 mm) gave 95 g of ethyl 2-benzylideneamino-2-methyl-4-[(tetrahydro-2H-pyran-2-yl)oxy]butyrate which was homogeneous by vpc and gave acceptable NMR and mass spectra. It was stored under N₂ in the refrigerator and was used without further purification.

67D.
2-Benzylamino-2-methyl-4-[(tetrahydro-2H-pyran-2-yl)oxy]butanol

A solution of ethyl 2-benzylideneamino-2-methyl-4-[(tetrahydro-2H-pyran-2-yl)oxy]butyrate (67C, 100.0 g, 0.3 mol) in THF (100 mL) was added slowly to a suspension of lithium aluminum hydride (Morton Thiokol, Inc. -Alfa Products, 22.77 g, 0.6 mol) rapidly stirred in dry THF (1 L) at such a rate to maintain a gentle reflux. After the addition was complete the mixture was refluxed for 4 h. The reaction mixture was cooled and treated successively with H₂O (23 mL), 15N NaOH (23 mL) and H₂O (45 mL). The solid was removed by filtration and washed with THF (200 mL). The organic layers were combined and concentrated by rotary evaporation to give 2-benzylamino-2-methyl-4-[(tetrahydro-2H-pyran-2-yl)oxy]butanol (81.1 g, 92.0%) as a thick oil which was used without further purification.

67E. 2-Benzylamino-2-methyl-1,4-butanediol

The crude 2-benzylamino-2-methyl-4-[(tetrahydro-2H-pyran-2-yl)oxy]butanol (67D, 80.1 g, 0.273 mol) was dissolved in 3N HCl (128 mL). After 5 min the mixture was washed with Et₂O (200 mL). The aqueous solution was concentrated by rotary evaporation to give a thick oil which was cooled and basified with excess 50% NaOH. The oily amine which formed was extracted with Et₂O (3×200 mL). The Et₂O extracts were combined and concentrated to give 63.6 of a thick oil. Distillation gave 49.8 g (94%) of 2-benzylamino-2-methyl-1,4-butanediol as a pale yellow oil, (bp 168°–170°/0.35 mm), C,H,N).

67F. 2-Amino-2-methyl-1,4-butanediol hydrochloride

2-Benzylamino-2-methyl-1,4-butanediol (67E, 31.08 g, 0.149 mol) was dissolved in 95% EtOH (240 mL) containing concentrated HCl (21 mL, 0.25 mol) and 5% Pd/C (10.0 g) and reduced in a Parr apparatus at 40 psi over 37 h at RT. The catalyst was then removed by filtration and the solvent removed by rotary evaporation (bath at 60°) to give 20.91 g of 2-amino-2-methyl-1,4-butanediol hydrochloride (90.2%) as a clear, thick, colorless oil with acceptable NMR and mass spectra. It was used without further purification. This compound has been reported as its acetetate salt (G. Cardillo et al., *Chem. Commun.* 13808, 1982), but no data was given. Attempts to duplicate the latter porcedure were unsuccessful.

67G.
2-Methyl-2[[(7-methyl-7H-benzo[c]carbazol-10-yl)methyl]amino]-1,4-butanediol hydrochloride·0.2 H₂O To a RB flask was added 2-amino-2-methyl-1,4-butanediol hydrochloride (67F), an equimolar amount of sodium methoxide (MCB) and CH₃OH (100 mL). After warming, the solvent was removed by rotary evaporation, and after addition of 7-methyl-7H-benzo[c]carbazole-10-carbaldehyde (4B), the reaction run following the normal reductive amination procedure outlined in Example 1 to give a 12.7% yield of 2-methyl-2-[[(7-methyl-7H-benzo[c]carbazol-10-yl)methyl]amino]-1,4-butanediol hydrochloride·0.2 H₂O, mp 209°–210°, (EtOH/Et₂O), (C,H,N,Cl).

EXAMPLE 68
2-[[(10-Methyl-10H-[1]benzothieno[3,2-b]indol-6-yl)methyl]amino]-2-methyl-1,3-propanediol

68A. 10-Methyl-10H-[1]benzothieno[3,2-b]indole

Using the procedure outlined in Example 34A except that dimethyl sulfate was used as the alkylating agent, 10H-[1]benzothieno[3,2-b]indole (prepared by the method of K. E. Chippendale and B. Iddon, *JCS Perkin Tans. I,* 2023 (1972)) gave a 91.9% yield of 10-methyl-10H-[1]enzothieno[3,2-b]indole, mp 175°–176°, (CH₂Cl₂/hexane), (C,H,N,S).

68B. 10-Methyl-10H-[1.benzothieno[3,2-b]indole-6-carbaldehyde·0.1 H₂O

68C. 10-Methyl-10H-[1]benzothieno[3,2-b]indole-3-carbaldehyde

10-Methyl-10H-[1]benzothieno[3,2-b]indole (68A) was formylated according to the procedure of A. Rieche et al., *Chem. Ber.* 93, 88 (1960) to give a low yield of a mixture of two aldehyes. Chromatography(SiO₂/PhCH₃) gave a 6.7% yield of 10-methyl-10H-[1]benzothieno[3,2-b]indole-6-carbaldehyde·0.1 H₂O (68B), mp 128°–130°, (CH₂Cl₂/hexane), (C,H,N,S,), R$_f$=0.39 and a 22.3% yield of 10-methyl--10H-[1]benzothieno[3,2-b]indole-3-carbaldehyde (68C), mp 188°189.5°, (PhCH₃/hexane), (C,H,N,S), R$_f$=0.11.

68D.
2-[[(10-Methyl-10H-[1]benzothieno[3,2-b]indol-6-yl)methyl]amino]-2-methyl-1,3-propanediol hydrochloride Using the procedure outlined in Example 1, 10-methyl-10H-[1]benzothieno[3,2-b]indole-6-carbaldehyde (68B) and 2-amino-2-methyl-1,3-propanediol (Aldrich) gave a 26.9% yield of 2-[[(10-methyl-10H-[1]benzothieno[3,2-b]indol-6-yl)methyl]amino]-2-methyl-1,3-propanediol hydrochloride, mp 249.5°–250°, (CH₃OH/Et₂O), (C,H,N,S,Cl).

EXAMPLE 69
2-[[(10-Methyl-10H-[1]benzothieno[3,2-b]indol-3-yl)methyl]amino]-2-methyl-1,3-propanediol hydrochloride Using the procedure outlined in Example, 1, 10-methyl-10H-[1]benzothieno[3,2-b]indole-3-carbaldehyde (68C) and 2-amino-2-methyl-1,3-propanediol (Aldrich) gave a 39.4% yield of 2-[[(10-methyl-10H-[1]benzothieno-[3,2-b]indol-3-yl)methyl]amino[-2-methyl-1,3-propanediol hydrochloride, mp 258.5°–259.5°, (CH₃OH/Et₂O), (C,H,N,S,Cl).

ANTITUMOR SCREENING RESULTS

Methods for evaluating the antitumor activity of these compounds are essentially those used in the Tumor Panel by the Developmental Therapeutics Program, Division of Cancer Treatment, National Cancer Institute, A. Goldin, et al., *Methods in Cancer Research,* Vol. XVI, p. 165, Academic Press (1979). Some modifications, in dose level and schedule have been made to increase the testing efficiency.

EXAMPLE 70

Lymphocytic Leukemia P388 Test

Male $CD2_2$-$F_1$ mice, weighing 20±3 g, were used for this test. Control and test animals were injected intraperitoneally with a suspension of ~$10^6$ viable P388 tumor cells on day 0. In each test, several dose levels which bracketed the $LD_{20}$ of the compound were evaluated; each dose level group contained six animals. The test compounds were prepared either in physiologic saline containing 0.05% Tween 80 or distilled water containing 5% dextrose and were administered intraperitoneally on days 1, 5, and 9 relative to tumor implant. Doses were on a mg/kg basis according to individual animals' body weights. The day of death for each animal was recorded, the median identified for each group and the ratios of median survival time for treated (T)/control (C) groups were calculated. The criterion for activity is $T/C \times 100 \geq 120\%$. Results of P388 testing are summarized in Table I.

TABLE I

| Compound of Formula | Optimal Dose (mg/kg) | T/C × 100% (Excluding 30 Day Survivors) | 30 Day Survivors | $LD_{20}$ (mg/kg) |
| --- | --- | --- | --- | --- |
| 1 | 65 | +225 | 1/6 | 35 |
| 2B | 100 | +250 | 1/6 | 50 |
| 3B | 20 | +230 | 2/6 | 10 |
| 4E | 80 | >+300 | 6/6 | 55 |
| 5B | 125 | +255 | 4/6 | 100 |
| 6B | 70 | +250 | 2/6 | 35 |
| 7B | 450 | +158 | 0/6 | 400 |
| 9B | 110 | +205 | 0/6 | 140 |
| 10 | 400 | +290 | 2/5 | 320 |
| 12B | 290 | +156 | 0/6 | 200 |
| 13B | 20 | +155 | 0/6 | 20 |
| 15C | 100 | +227 | 1/6 | 120 |
| 17C | 120 | +250 | 2/6 | 80 |
| 18C | 175 | +130 | 0/6 | 150 |
| 19B | 2.5 | +145 | 0/6 | 1.0 |
| 20B | 200 | +225 | 0/6 | 175 |
| 21B | 360 | +170 | 0/6 | 360 |
| 23B | 300 | +120 | 0/6 | 350 |
| 24 | 65 | +266 | 0/6 | 50 |
| 25B | 250 | +130 | 0/6 | 100 |
| 26B | 450 | +140 | 0/6 | 250 |
| 32 | 50 | +290 | 3/6 | 50 |
| 33 | 10 | +160 | 0/6 | 10 |
| 34C | 60 | +109 | 5/6 | 45 |
| 37B | 225 | +135 | 0/6 | 200 |
| 38C | 150 | +120 | 0/6 | 125 |
| 39C | 90 | +225 | 0/6 | 60 |
| 43B | 135 | +220 | 0/6 | 105 |
| 44C | 140 | +260 | 2/6 | 100 |
| 45B | 110 | +245 | 2/6 | 60 |
| 46B | 500 | +265 | 4/6 | 425 |
| 47B | 150 | +255 | 0/6 | 75 |
| 50C | 150 | +136 | 5/6 | 75 |
| 52 | 55 | +145 | 0/6 | 50 |
| 53D | 300 | +135 | 0/6 | 125 |
| 55D | 100 | +120 | 0/6 | 100 |
| 56B | 125 | +215 | 0/6 | 125 |

EXAMPLE 71

Formulation Examples

A. TABLET

| | |
| --- | --- |
| Compound of formula (I) | 500.0 mg |
| Pregelatinized Corn Starch | 60.0 mg |
| Sodium Starch Glycolate | 36.0 mg |
| Magnesium Stearate | 4.0 mg |

The compound of formula (I) is finely ground and intimately mixed with the powdered excipients, pregelatinized corn starch and sodium starch glycolate. The powders are wetted with purified water to form granules. The granules are dried and mixed with the magnesium stearate. The formulation is then compressed into tablets weighing approximately 600 mg each.

B. TABLET

| | |
| --- | --- |
| Compound of formula (I) | 500.0 mg |
| Corn Starch | 70.0 mg |
| Lactose | 83.8 mg |
| Magnesium Stearate | 4.2 mg |
| Polyvinylpyrrolidone | 14.0 mg |
| Stearic Acid | 28.0 mg |

The compound of formula (I) is finely ground and intimately mixed with the powdered excipients, corn starch and lactose. The powders are wetted with a solution of polyvinylpyrrolidone dissolved in a mixture of purified water and denatured alcohol to form granules. The granules are dried and mixed with the powdered stearic acid and magnesium stearate. The formulation is then compressed into tablets weighing approximately 700 mg each.

C. CAPSULES

| | |
| --- | --- |
| Compound of formula (I) | 500.0 mg |
| Corn Starch | 50.0 mg |
| Magnesium Stearate | 3.0 mg |

The finely divided compound of formula (I) is mixed with powdered corn starch and wetted with denatured alcohol to densify the powder. The dried powder is mixed with stearic acid and filled into hard-shell gelatin capsules.

D. SYRUP

| | |
| --- | --- |
| Compound of formula (I) | 250.0 mg |
| Ethanol | 250.0 mg |
| Glycerin | 500.0 mg |
| Sucrose | 3,500.0 mg |
| Flavoring Agent | q.s. |
| Coloring Agent | q.s. |
| Preserving Agent | 0.1% |
| Purified Water q.s to | 5.0 mL |

The compound of formula (I) is dissolved in the ethanol, glycerin, and a portion of the purified water. The sucrose and preserving agent are dissolved in another portion of hot purified water, and then the coloring agent is added and dissolved. The two solutions are mixed and cooled before the flavoring agent is added. Purified water is added to final volume. The resulting syrup is throughly mixed.

E. IV INJECTION

| | |
| --- | --- |
| Compound of formula (I) | 5.0 mg |
| Glycerin | q.s. for isotonicity |
| Preservative | 0.1% |
| Hydrochloric Acid or Sodium Hydroxide | as needed for pH adjustment |
| Water for Injection | q.s. to 1 mL |

The compound of formula (I) and preservative is added to the glycerin and a portion of the water for injection. The pH is adjusted with hydrochloric acid or sodium hydroxide. Water for injection is added to final volume and solution is complete after thorough mixing. The solution is sterilized by filtration through a 0.22 micrometer membrane filter and aseptically filled into sterile 10 mL ampules or vials.

What is claimed is:

1. A compound of formula (I)

  (I)

or acid addition salts thereof;
wherein Ar is phenanthro thiophen optionally substituted by one or two substituents selected from halogen; cyano $C_{1-4}$ alkyl or $C_{1-4}$ alkoxy, each optionally substituted by hydroxy or $C_{1-2}$ alkoxy, each optionally substituted by hydroxy or $C_{1-2}$ alkoxy; halogen-substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the heterocyclic ring is optionally substituted by a group $NR^3R^4$ containing not more than 5 carbon atoms wherein $R^3$ and $R^4$ are the same or different and each is a $C_{1-3}$ alkyl group;
$R^1$ contains not more than eight carbon atoms and is a group

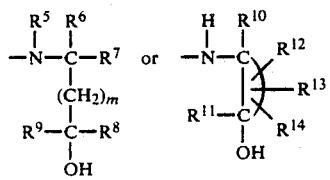

wherein
m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

2. A compound of claim 1 wherein $R^1$ is

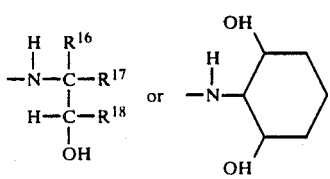

wherein $R^{16}$ is $CH_2OH$, $CH(CH_3)OH$ or $CH_2CH_2OH$; $R^{17}$ is hydrogen, $C_{1-3}$ alkyl or $CH_2OH$; $R^{18}$ is hydrogen or methyl.

3. A compound claim 2 wherein
$R^{16}$ is $CH_2OH$ or $CH(CH_3)OH$ and $R^{17}$ is hydrogen, methyl, ethyl or $CH_2OH$.

4. A compound of claim 1 wherein $R^1$ is a diol of the structure

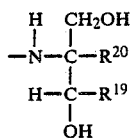

wherein $R^{19}$ is hydrogen or methyl and $R^{20}$ is hydrogen, methyl or ethyl.

5. A compound of claim 4 wherein $R^{20}$ is methyl.

6. 2-methyl-2-[[(phenanthro-[2,3-b]thiophen-7-yl)methyl]amino]-1,3-propanediol.

7. A pharmaceutically acceptable acid addition salt of claim 6.

8. A method for reducing the number of cells of a solid or ascitic tumor susceptible to such reduction in a mammal bearing said tumor comprising the administration of an effective tumor cell number reducing amount of a compound of formula (I)

ArCH$_2$R$^1$  (I)

or acid addition salts thereof;
wherein Ar is phenanthro thiophen optionally substituted by one or two substituents; selected from halogen; cyano; $C_{1-4}$ alkyl or $C_{1-4}$ alkoxy, each optionally substituted by hydroxy or $C_{1-2}$ alkoxy; halogen-substituted $C_{1-2}$ alkyl or $C_{1-2}$ alkoxy; a group $S(O)_nR^2$ wherein n is an integer 0,1or 2 and $R^2$ is $C_{1-2}$ alkyl optionally substituted by hydroxy or $C_{1-2}$ alkoxy; or the heterocyclic ring is optionally substituted by a group $NR^3R^4$ containing not more than 5 carbon atoms wherein $R^3$ and $R^4$ are the same or different and each is a $C_{1-3}$ alkyl group;
$R^1$ contains not more than eight carbon atoms and is a group

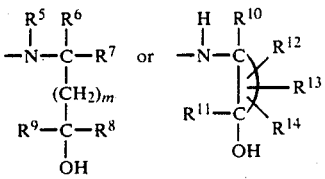

wherein
m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

is a five- or six-membered saturatred carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

9. A method of claim 8 wherein
$R^1$ is

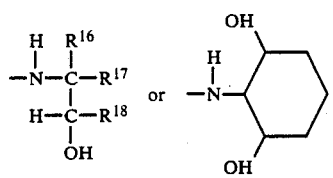

$R^{16}$ is $CH_2OH$, $CH(CH_3)OH$ or $CH_2CH_2OH$; $R^{17}$ is hydrogen, $C_{1-3}$ alkyl or $CH_2OH$;

$R^{18}$ is hydrogen or methyl.

10. A method of claim 9 wherein $R^{16}$ is $CH_2OH$ or $CH(CH_3)OH$ and $R^{17}$ is hydrogen, methyl, ethyl or $CH_2OH$.

11. A method of claim 8 wherin $R^1$ is a diol of the stucture

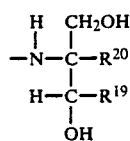

wherein $R^{19}$ is hydrogen or methyl and $R^{20}$ is hydrogen, methyl or ethyl.

12. A method of claim 11 wherein $R^{20}$ is methyl.

13. A method of claim 12 wherein the compound of formula (I) is a methanesulfonic, hydrochloric, ethanesulfonic, lactic, citric or isethionic acid addition salt.

14. A method of claim 8 wherein the tumor is an ascitic tumor.

15. The method of claim 8 in which the compound or salt of formula (I) is 2-methyl-2-[[(phenanthro[2,3-b]thiophen-7-yl)methyl]amino]-1,3-propanediol or a pharmaceutically acceptable acid addition salt thereof.

16. A pharmaceutical formulation containing a compound of formula (I)

$$ArCH_2R^1 \qquad (I)$$

or acid addition salts thereof; wherein Ar is phenanthro[2,3-b]thiophen optionally substituted by one or two substituents; selected from halogen; cyano; $C_{1-4}$ alkyl or $C_{1-4}$ alkoxy, each optionally substituted by hydroxy or $C_{1-2}$ alkoxy; halogn-substituted $C_{1-2}$ alkyl or $C_{1-2}$ alkoxy; a group $S(O)_n R^2$ wherein n is an integer 0, 1 or 2 is $C_{1-2}$ alkyl optionally substituted by hydroxy or $C_{1-2}$ alkoxy; or the heterocyclic ring is optionally substituted by a group $NR_3R_4$ containing not more than 5 carbon atoms wherein $R^3$ and $R^4$ are the same or different and each is a $C_{1-3}$ alkyl group;

$R^1$ contains not more than eight carbon atoms and is a group

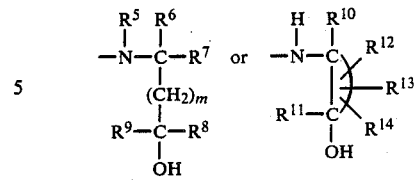

wherein
m is 0 or 1;
$R^5$ is hydrogen;
$R^6$ are $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

$$-C\frown C-$$

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl with a pharmaceutically acceptable carrier in the form of a tablet, capsule, syrup or injection.

17. A pharmaceutical formulation of claim 16 wherein $R^1$ is

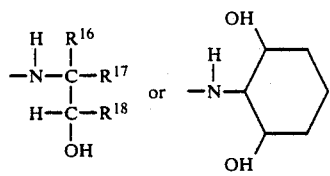

$R^{16}$ is $CH_2OH$, $CH(CH_3)OH$ or $CH_2CH_2OH$; $R^{17}$ is hydrogen, $C_{1-3}$ alkyl or $CH_2OH$;
$R^{18}$ is hydrogen or methyl.

18. A pharmaceutical formulation of claim 17 wherein $R^{16}$ is $CH_2OH$ or $CH(CH_3)OH$ and $R^{17}$ is hydrogen, methyl, ethyl or $CH_2OH$.

19. A pharmaceutical formulation of claim 17 wherein $R^1$ is a diol of the structure

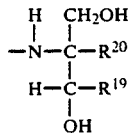

wherein $R^{19}$ is hydrogen or methyl and $R^{20}$ is hydrogen, methyl or ethy.

20. A pharmaceutical formulation claim 19 wherein $R^{20}$ is methyl.

21. The composition of claim 16 in which the compound or salt of formula (I) is 2-methyl-2-[[(phenantro[2,3-b]thiophen-7-yl)methyl]amino]-1,3-propanediol or a pharmaceutically acceptable acid addition salt thereof.

* * * * *